US012767745B2

(12) United States Patent
Willner et al.

(10) Patent No.: US 12,767,745 B2
(45) Date of Patent: Oct. 20, 2026

(54) DENTAL LIGHT-CURABLE COMPOSITION AND CORRESPONDING RESTORATIONS, PRODUCTION METHODS AND USES

(71) Applicant: VOCO GmbH, Cuxhaven (DE)

(72) Inventors: Alexander Willner, Cuxhaven (DE); Christoph Hahn, Wurster Nordseeküste (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 916 days.

(21) Appl. No.: 18/145,168

(22) Filed: Dec. 22, 2022

(65) Prior Publication Data

US 2023/0192925 A1 Jun. 22, 2023

(30) Foreign Application Priority Data

Dec. 22, 2021 (DE) ......................... 102021134260.0

(51) Int. Cl.

| | |
|---|---|
| ***C08F 220/12*** | (2006.01) |
| ***A61K 6/16*** | (2020.01) |
| ***A61K 6/17*** | (2020.01) |
| ***A61K 6/62*** | (2020.01) |
| ***A61K 6/80*** | (2020.01) |
| ***C08K 3/11*** | (2018.01) |
| ***C08K 3/36*** | (2006.01) |

(52) U.S. Cl.

CPC .............. *C08F 220/12* (2013.01); *C08K 3/11* (2018.01); *C08K 3/36* (2013.01); *A61K 6/16* (2020.01); *A61K 6/17* (2020.01); *A61K 6/62* (2020.01); *A61K 6/80* (2020.01); *C08K 2201/005* (2013.01)

(58) Field of Classification Search

CPC .............. A61K 6/16; A61K 6/17; A61K 6/62; A61K 6/80

See application file for complete search history.

(56) References Cited

U.S. PATENT DOCUMENTS

| | | | |
|---|---|---|---|
| 4,115,346 A | 9/1978 | Gross | |
| 4,323,348 A | 4/1982 | Schmitz-Josten | |
| 4,744,827 A | 5/1988 | Winkel | |
| 4,744,828 A | 5/1988 | Winkel | |
| 4,952,614 A | 8/1990 | Reiners | |
| 5,847,025 A | 12/1998 | Moszner | |
| 6,365,771 B1 | 4/2002 | Suzuki | |
| 2006/0252845 A1 | 11/2006 | Ruppert | |
| 2007/0142496 A1 | 6/2007 | Grundler | |
| 2008/0167399 A1 | 7/2008 | Utterodt | |
| 2009/0036565 A1 | 2/2009 | Utterodt | |
| 2015/0272833 A1 | 10/2015 | Toriyabe | |
| 2016/0113846 A1 | 4/2016 | Willner | |
| 2017/0224591 A1 | 8/2017 | Vogel | |
| 2019/0192386 A1 | 6/2019 | Fukudome | |
| 2023/0059534 A1* | 2/2023 | Busch | A61K 6/887 |

FOREIGN PATENT DOCUMENTS

| | | |
|---|---|---|
| CA | 2425953 | 10/2002 |
| CN | 113730264 | 12/2021 |
| DE | 2419887 | 11/1974 |
| EP | 1563821 | 8/2005 |
| WO | 2021/148667 | 7/2021 |

OTHER PUBLICATIONS

Watts, D.C., et al., “Determination of polymerization shrinkage kinetics in visible-light-cured materials: methods development,” Dental Materials, Oct. 1991, vol. 7, pp. 281-287.

De Gee, A.J., et al., “Occlusal wear simulation with the ACTA wear machine,” J. Dent. Suppl. 1, 1994, vol. 22; pp. S21-S27.

* cited by examiner

*Primary Examiner* — Kregg T Brooks
*Assistant Examiner* — David R. Foss
(74) *Attorney, Agent, or Firm* — DUANE MORRIS LLP; Gregory M. Lefkowitz; Brandon A. Chan

(57) ABSTRACT

What is described is a dental light-curable composition for elective production of a visible restoration in the anterior region or for filling of a cavity in the posterior region, comprising a total amount (A) of free-radically polymerizable monomers, where this total amount (A) consists of one, two, three or more than three free-radically polymerizable monomers and has a refractive index $n_{A, 470\ nm}$ in the range from 1.470 to 1.560, a total amount (B1) of nonaggregated and nonagglomerated inorganic filler particles having a particle size in the range from 7 to 70 nm, where this total amount (B1) has a refractive index $n_{B1, 470\ nm}$ in the range from 1.460 to 1.570 and where this total amount (B1) is in the range from 10 to 30 percent by volume, based on the overall dental light-curable composition, a total amount (B2) of inorganic filler particles having a particle size in the range from 0.12 μm to 10 μm, where this total amount (B2) has a refractive index $n_{B2, 470\ nm}$ in the range from 1.450 to 1.560, and a total amount (C) of photoinitiators.

15 Claims, No Drawings

DENTAL LIGHT-CURABLE COMPOSITION AND CORRESPONDING RESTORATIONS, PRODUCTION METHODS AND USES

CROSS REFERENCE TO RELATED APPLICATIONS

This application claims priority to German Patent Application No. 102021134260.0, filed on Dec. 22, 2021, the entire contents of which are incorporated herein by reference.

The present invention relates to a dental light-curable composition suitable for elective production of a visible restoration in the anterior region or for filling of a cavity in the posterior region. The dental light-curable composition of the invention may thus electively serve various purposes, which would previously have been considered by the dental expert to be barely reconcilable.

The invention additionally relates to a dental restoration or to a cured dental material obtainable by light-curing of a dental light-curable composition of the invention. The dental restoration of the invention is preferably—and electively—a visible dental restoration in the anterior region or a filling of a cavity in the posterior region.

The present invention additionally relates to a method of producing a dental light-curable composition of the invention.

The present invention also relates to the use of total amounts of particular free-radically polymerizable monomers and inorganic filler particles for production of a dental light-curable composition. The dental light-curable composition produced is preferably a composition of the invention.

The invention also relates to a dental light-curable composition of the invention for use in a method of surgical or therapeutic treatment of the human or animal body and/or for use in a diagnostic method performed on the human or animal body. Preference is given here to a specific application, electively in a therapeutic method for temporary or permanent visible restoration in the anterior region or in a therapeutic method for temporary or permanent filling of a cavity in the posterior region. Further preferred specific applications will be apparent from the appended claims and the description that follows.

The invention also relates to a method of producing a visible restoration in the anterior region or for filling of a cavity in the posterior region.

The invention is defined in the appended claims. Preferred aspects of the present invention will, moreover, be apparent from the description that follows, including the examples.

Where particular configurations are referred to as being preferred for one aspect of the invention (composition; restoration or dental material; production method; use; (specific) application in a method; method of producing a restoration or of filling a cavity), the corresponding details are in each case also applicable to the other aspects of the present invention, mutatis mutandis. Preferred individual features of aspects of the invention (as defined in the claims and/or disclosed in the description) are combinable with one another and are preferably combined with one another, unless the opposite is apparent to the person skilled in the art from the present text in the specific case.

Dental light-curable compositions are already known from the prior art. Modern dental light-curable compositions frequently include an amount of free-radically polymerizable monomers, microfillers and nanofillers. Further constituents of modern dental light-curable compositions are photoinitiators and colorants (for example color pigments).

Corresponding compositions are also referred to as "nano-hybrid composites". Scientific product information relating to the nano-hybrid composite GrandioSO that has been published by the present patentee summarizes significant aspects and considerations in the present technical field; it refers to customary methods of determination. The scientific product information is available on the Internet: https://www.voco.dental/de/portaldata/1/resources/products/scientific-compendiums/de/grandioso_scc_de.pdf.

Dental light-curable compositions are also numerously disclosed in the patent literature.

EP 2 987 480 A1 (Ivoclar Vivadent AG) discloses light-curing dental composites with increasing opacity.

EP 2 902 007 A1 (Tokuyama Dental Corporation) discloses a "dental filling repairing material".

EP 3 508 190 A1 discloses a "photocurable composition".

EP 3 854 374 A1 and WO 2021/148667 A1 (Ivoclar Vivadent AG) disclose an "aesthetic dental filling material with high depth of cure".

The four aforementioned patent documents each disclose specific refractive indices for the monomer mixture used and for the fillers used.

CN 1 13 730 264 A discloses a "Dental gradient color resin ceramic repair material and preparation method thereof".

EP 2 987 480 A1 discloses that the translucence of the dental material disclosed therein is affected by the refractive indices of the monomers and of the fillers. The translucence of an (uncured) dental light-curable composition is crucial for depth of cure (cf. EP 2 987 480 A1 again). A high depth of cure is required if, for example, deep cavities in the posterior region are to be filled with a dental light-curable composition.

In the light of the prior art, the dental expert will try to configure a dental light-curable composition in such a way that the refractive indices of monomer and filler vary only slightly from one another.

At the same time, however, little attention has been paid until now to the refractive indices of the macro- or microfillers. With regard to the nanofillers present in modern dental light-curable compositions, there was a prevalent conviction that the refractive indices thereof are not particularly relevant. For instance, it is apparent even from the already cited EP 2 902 007 A1 that nanofillers having an average particle size of less than 0.07 μm do not appear to be usable. It was said that the particle size of these nanoparticles is less than the wavelength of visible light, such that they appear transparent irrespective of their refractive index. This is in turn said to have the effect that it is difficult to achieve a cured product corresponding in its appearance to a natural tooth.

Particularly for visible restorations in the anterior region, it is important for aesthetic reasons that even a thin layer of a cured dental light-curable composition used as restoration material is no longer excessively translucent. Instead, a certain opacity is required in order that the dental restoration gives maximum perfection of simulation of the appearance of natural tooth material.

The overall outcome for the dental expert, considering firstly the technical subsector of visible restorations in the anterior region and secondly the separate technical subsector of cavity filling in the posterior region, is thus a number of demands that seemed to be irreconcilable to date. Probably for that reason, there have to date been no dental light-curable compositions on the market that can be used with convincing success in each case electively for production of a visible restoration in the anterior region or for filling of a cavity in the posterior region. Said demands that were assumed to be irreconcilable to date can be summarized as follows:

A dental light-curable composition for production of a visible restoration in the anterior region must be capable of giving the aesthetic impression of a front tooth after curing.

A dental light-curable composition for filling a deep cavity (for example of cavity depth >3 mm) in the posterior region must have high depth of cure in order that the composition after filling into said cavity can indeed be cured completely and in one step. The dental light-curable composition must therefore have correspondingly high translucence in the uncured state. It should be noted in this respect that, in dental practice, virtually exclusively colored dental light-curable compositions are produced for practical purposes, especially in the case of planned use even in the anterior region. It will be apparent that the type and amount of substances used for coloring have effects on depth of cure and translucence. For the purposes of fair comparisons, therefore, firstly uncolored dental light-curable compositions (base compositions) and dental light-curable compositions that have been colored each in an identical manner are to be compared with one another.

A dental light-curable composition for production of a visible restoration in the anterior region and for filling of a cavity in the posterior region must in each case have excellent physical and mechanical properties, as described more particularly by the parameters of modulus of elasticity (as a measure of material strength or resistance to deformation and fracture), ACTA abrasion (as a measure of loss of substance through wear) and polymerization shrinkage (as a measure for material shrinkage on curing). It is insufficient here that only individual selected requirements on mechanical properties are met. Instead, a dental light-curable composition used in practice must be resistant to mechanical (tensile) stresses (characterized inter alia by a minimum value for modulus of elasticity), withstand wear forces over a long period (characterized inter alia by a maximum value for ACTA abrasion), and additionally have only low shrinkage caused by the curing (characterized inter alia by a maximum value of polymerization shrinkage).

It was a primary object of the present invention to specify a dental light-curable composition which, in spite of the above-outlined assessments and difficulties, is capable both of forming a visible restoration in the anterior region and capable of filling a cavity in the posterior region. The dental light-curable composition to be specified was thus to be able to be used, according to the requirements of the individual case, electively for one or the other purpose. In this way, the dentist implementing treatment is to be given the option of using a single dental light-curable composition to take two different therapeutic measures for which the use of two different dental light-curable compositions was necessary to date.

Moreover, a corresponding dental restoration or a corresponding cured dental material was to be specified, which is obtainable by light curing of such a dental light-curable composition. It should be noted here that, typically and with preference, light curing takes place using light within a wavelength range from 450 nm to 490 nm, i.e. using blue light.

Moreover, a corresponding method of producing an (inventive) dental light-curable composition was to be specified. In addition, it should be taken into account that the dental light-curable composition to be specified is suitable for use in the above-discussed surgical and therapeutic methods, i.e. is suitable more particularly for specific use in a therapeutic method of temporary or permanent visible restoration in the anterior region or in a therapeutic method of temporary or permanent filling of a cavity in the posterior region.

With regard to a corresponding method to be specified for production of a visible restoration in the anterior region or for filling of a cavity in the posterior region, it should be taken into account that the curing of the dental light-curable composition applied should preferably be effected by irradiation with light in the wave-length range from 450 nm to 490 nm (blue light).

The primary object of the present invention is achieved by a dental light-curable composition according to the appended claim 1. The primary object is thus achieved by a dental light-curable composition for elective production of a visible restoration in the anterior region or for filling of a cavity in the posterior region, comprising a total amount (A) of free-radically polymerizable monomers, where this total amount (A) consists of one, two, three or more than three free-radically polymerizable monomers and has a refractive index $n_A$, 470 nm in the range from 1.470 to 1.560, a total amount (B1) of nonaggregated and nonagglomerated inorganic filler particles having a particle size in the range from 7 to 70 nm, where this total amount (B1) has a refractive index $n_{B1,\ 470\ nm}$ in the range from 1.460 to 1.570 and where this total amount (B1) is in the range from 10 to 30 percent by volume, based on the overall dental light-curable composition, a total amount (B2) of inorganic filler particles having a particle size in the range from 0.12 μm to 10 μm, where this total amount (B2) has a refractive index $n_{B2,\ 470\ nm}$ in the range from 1.450 to 1.560, and a total amount (C) of photoinitiators, where the following condition applies to the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.025<n_{A,470\ nm}<n_{B1,470\ nm}+0.030$$

and where the following condition applies to the refractive indices of the total amount (A) of free-radically polymerizable monomers and the total amount (B2) of inorganic filler particles having a particle size in the range from 0.12 μm to 10 μm:

$$n_{B2,470\ nm}-0.015<n_{A,470\ nm}<n_{B2,470\ nm}+0.040$$

and where the following condition applies to the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.020<n_{B1,470\ nm}<n_{B2,470\ nm}+0.035.$$

The invention is based on a whole series of interconnected considerations, the overall effect of which is that the difficulties outlined above were able to be overcome.

The inventors first noted that a dental light-curable composition intended to be suitable for filling of a cavity in the posterior region must have excellent depth of cure, as already taken into account in a similar manner in the design of dental composites that have been tailored for the purpose of producing cavity fillings in the posterior region.

The inventors additionally took into account that the cured restoration, i.e. the dental light-curable composition after curing, typically after irradiation with blue light, must have only low translucence. This is because only cured dental materials having low translucence are capable of giving the aesthetic impression of a front tooth and are thus suitable as visible restoration in the anterior region.

The inventors additionally took into account that the cured restoration, i.e. the dental light-curable composition after curing, must meet the high mechanical demands that are placed on dental materials.

The features mentioned relating to depth of cure and translucence, and the mechanical properties after curing, reflect the extremely different demands that should be taken into account firstly in the filling of a cavity in the posterior region and secondly in the production of a visible restoration in the anterior region.

The present invention has succeeded in fulfilling all three demands with a single dental light-curable composition. For this purpose, in turn, the composition of suitable materials is crucial, as defined above.

According to the invention, the dental light-curable composition comprises a total amount (A) of free-radically polymerizable monomers, where this total amount (A) consists of one, two, three or more than three free-radically polymerizable monomers and has a refractive index $n_{A,\ 470\ nm}$ in the range from 1.470 to 1.560 (because the monomer(s) is/are correspondingly selected and matched to one another in terms of amount).

For the understanding of the present invention, it is important here to note that the refractive index is determined as specified at a wavelength of 470 nm, i.e. within the wavelength range of blue light as typically used in light curing. The present invention thus, by contrast with the customary approach of the dental expert to date, takes particular account of the fact that light curing in dental practice is regularly effected using blue light. What is therefore important for success of the present invention is essentially that the materials used and the properties thereof are selected with regard to the curing method and hence with regard to the customary use of blue light. It will be apparent to the person skilled in the art that every refractive index $n_{A,\ 470\ nm}$ (i.e. a refractive index that has been determined at a wavelength of 470 nm, i.e. in the range of blue light) also corresponds to a refractive index which is determined (for example) at the wavelength of yellow light (for example the sodium D line, 589 nm). As stated, the inventive selection of the free-radically polymerizable monomers is made, however, in such a way that the total amount (A) has the desired refractive index $n_{A,\ 470\ nm}$.

The dental light-curable composition of the invention, as well as the total amount of free-radically polymerizable monomers, additionally comprises the above-defined total amounts (B1) and (B2) of inorganic filler particles.

In particular, the composition of the invention comprises a total amount (B1) of nonaggregated and nonagglomerated inorganic filler particles having a particle size in the range from 7 to 70 nm, where this total amount (B1) has a refractive index $n_{B1,\ 470\ nm}$ in the range from 1.460 to 1.570. What is thus crucial in turn is the refractive index of the total amount (B1) in the case of a measurement with a wavelength of 470 nm, i.e. within the wavelength range of blue light. In the context of the present invention, it has been found that it is essential to the success of the invention that the following condition is applicable to the refractive indices of the total amount (A) of free-radically polymerizable monomers and the refractive indices of the total amount (B1) of nonaggregated and nonagglomerated inorganic filler particles having a particle size in the range from 7 to 70 nm:

$$n_{B1,470\ nm}-0.025<n_{A,470\ nm}<n_{B1,470\ nm}+0.030.$$

In other words, the refractive indices (each determined at 470 nm) of the total amount (A) and of the total amount (B1) should each be within a tightly defined range (1.470 to 1.560 or 1.460 to 1.570) and should additionally vary slightly from one another at most. There is no model in the prior art for taking account in this way of two refractive indices of nanofillers having a particle size in the range from 7 to 70 nm.

The present invention takes account of the fact that, contrary to expert assessments to date, the refractive index of said nanofillers also has a relevant effect on the properties of a dental composition before and after curing. Although the inventors of the present invention cannot yet give any definite scientific justification for the experimental success they have had, they assume at present that it is necessary to take account of the physical effects of Rayleigh scattering (i.e. the scattering of light at particles smaller than the wavelength of light used) as occur on irradiation of nanoparticles. Rayleigh scattering is highly dependent on the frequency of the light hitting the particles; for instance, blue light with a relatively high frequency is subject to more significant scatter than red light of low frequency. This scattering effect must thus be taken into account especially when blue light is used in order to be able to predict or even to predetermine the properties of a corresponding dental composition. The inventors assume that, when blue light is used, scattering effects, and additionally destructive interference effects, that take place at the nanoparticles of the total amount (B1) affect depth of cure in a composite. In order to reduce or to avoid adverse effects of nanofillers on translucence (in the uncured state) and hence on depth of cure, what is envisaged in accordance with the invention is that the total amount (B1) of nonaggregated and nonagglomerated inorganic (nano)filler particles is selected specifically with regard to its refractive index and—as already set out above—is matched to the refractive index of the total amount (A) of the free-radically polymerizable monomers, in order to establish maximum homogeneity of the refractive indices within the dental light-curable composition of the invention. In this way, a high depth of cure, preferably a depth of cure of 3.5 mm or more, is assured in accordance with the invention, naturally in interplay with the further constituents of the composition of the invention.

The dental light-curable composition of the invention comprises, as well as the total amount (A) of free-radically polymerizable monomers (as set out above) and the total amount (B1) of (nano)filler particles (as set out above), a total amount (B2) of inorganic filler particles having a particle size in the range from 0.12 μm to 10 μm, where this total amount (B2) has a refractive index $n_{B2,\ 470\ nm}$ in the range from 1.450 to 1.560. These are microfillers, the refractive indices $n_{B2,\ 470\ nm}$ of which (each determined at 470 nm) are matched to the above-discussed refractive indices of the total amount (A) of free-radically polymerizable monomers and the total amount (B1) of nanofillers. In particular, the following condition applies to the refractive indices of the total amount (A) of free-radically polymerizable monomers and the total amount (B2) of inorganic filler particles having a particle size in the range from 0.12 μm to 10 μm:

$$n_{B2,470\ nm}-0.015<n_{A,470\ nm}<n_{B2,470\ nm}+0.040.$$

What the invention does not involve is thus the mere balancing and suitable selection of the refractive indices of monomers on the one hand and filler particles (overall) on the other hand; instead, with regard to the filler particles, a precise distinction is made between the refractive indices of the total amount (B1) of (nano)filler particles (as further defined above) and the total amount (B2) of (micro)filler particles (as further defined above).

The present invention further takes into account that the refractive indices of the total amount (B1) of (nano)filler particles (as further defined above) and the total amount (B2) of (micro)filler particles (as further defined above) are also matched to one another. In particular, the following condition applies to the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.020<n_{B1,470\ nm}<n_{B2,470\ nm}+0.035.$$

This matching of the refractive indices of the particulate main constituents of the dental light-curable composition, i.e. of the nano- and microfiller particles in the total amounts (B1) and (B2), contributes to high homogeneity of the refractive indices within the dental light-curable composition of the invention and thus assures (even in the case of highly filled dental composites) a high depth of cure.

The invention thus involves considering all the refractive indices of the total amounts (A), (B1) and (B2) and selecting and matching them relative to one another such that light curing of dental light-curable compositions of the invention using light within a wavelength range from 450 nm to 490 nm (blue light) assures a high depth of cure. There is no model in the prior art for such threefold matching of the refractive indices of i) free-radically polymerizable monomers, ii) nanofiller particles and iii) microfiller particles.

As defined above and in the appended claims, the dental light-curable composition of the invention comprises a total amount (B1) of nonaggregated and nonagglomerated inorganic filler particles having a particle size in the range from 7 to 70 nm (nanofiller particles), where this total amount (B1) is in the range from 10 to 30 percent by volume, based on the overall dental light-curable composition.

It has been found that use of a high proportion by volume of nanofiller particles of at least 10 percent by volume, after curing of the composition of the invention, achieves excellent physical and mechanical properties. It has also been found that a high proportion of nanofiller particles of more than 30 percent by volume adversely affects the mechanical properties in many cases. The inventors have succeeded not only in identifying compositions that give the aesthetic impression of a front tooth (in particular, the translucence achieved after curing is excellent) and have high depth of cure. To wit, preferred compositions of the invention preferably have the following mechanical properties, determined by the respective methods of determination specified hereinafter:

a modulus of elasticity, determined from the slope in the linear-elastic region of the graph from the stress-strain diagram of the measurement of flexural strength by production and curing of test specimens with dimensions 2×2×25 mm analogously to the method described in ISO 4049:2019, of more than 10 GPa,
preferably of more than 11.5 GPa,
more preferably of more than 13 GPa,
and/or (preferably "and")
an ACTA abrasion, determined after curing by means of a wear simulation according to ISO/TS 14569-2 of less than 70 μm,
preferably of less than 60 μm,
more preferably of less than 55 μm,
and/or (preferably "and")
a polymerization shrinkage, determined by means of the bonded disk method and one hour after the exposure of test specimens with a light curing device having a radiation flux maximum at a wave-length in the range from 440 nm to 490 nm at a temperature of 23° C. and for a period of 40 s, of less than 2.0%,
preferably of less than 1.8%,
more preferably of less than 1.6%.

The expression "total amount (A) of free-radically polymerizable monomers" refers to the total amount of all free-radically polymerizable monomers present in the dental light-curable composition of the invention.

Aside from this total amount (A), there is thus no further amount of free-radically polymerizable monomers in the composition of the invention.

The "total amount (A) of free-radically polymerizable monomers" preferably comprises one, two or more monomers selected from the group consisting of 2-hydroxyethyl (meth)acrylate, 2-hydroxypropyl (meth)acrylate, 3-hydroxypropyl (meth)acrylate, 1,2-dihydroxypropyl (meth) acrylate, 1,3-dihydroxypropyl (meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth) acrylate, tripropylene glycol di(meth)acrylate, tetrapropylene glycol di(meth)acrylate, polypropylene glycol di(meth) acrylate, butane-1,4-diol di(meth)acrylate, butane-1,3-diol di(meth)acrylate, hexane-1,6-diol di(meth)acrylate, decane-1,10-diol di(meth)acrylate, dodecane-1,12-diol di(meth) acrylate, 2-hydroxypropyl 1,3-di(meth)acrylate, 3-hydroxypropyl 1,2-di(meth)acrylate, 2,2-bis[4-[3-(meth) acryloyloxy-2-hydroxypropoxy]phenyl]propane, 2,2-bis[4-(meth)acryloyloxyphenyl]propane, 2,2-bis[4-(meth) acryloyloxyethoxyphenyl]propane, 2,2-bis[4-(meth) acryloyloxydiethoxyphenyl]propane, 2,2-bis[4-(meth) acryloyloxytriethoxyphenyl]propane, 2,2-bis[4-(meth) acryloyloxytetraethoxyphenyl]propane, 2,2-bis[4-(meth) acryloyloxypentaethoxyphenyl]propane, 2,2-bis[4-(meth) acryloyloxydipropoxy-phenyl]propane, 2,2-bis[4-(meth) acryloyloxyethoxyphenyl]-2-[4-(meth) acryloyloxydiethoxyphenyl]propane, 2-[4-(meth) acryloyloxydiethoxyphenyl]-2-[4-(meth) acryloyloxytriethoxphenyl]propane, 2-[4-(meth)acryloyloxdipropoxyphenyl]-2-[4-(meth) acryloyloxytriethoxyphenyl]propane, 2,2-bis[4-(meth) acryloyloxyiso-propoxyphenyl]propane, 7,7,9-trimethyl-3,14-dioxa-4,13-dioxo-5,12-diazahexadecane 1,16-diox-ydi (meth)acrylate, 7,9,9-trimethyl-3,14-dioxa-4,13-dioxo-5,12-diazahexadecane 1,16-dioxydi(meth)acrylate, neopentyl glycol di(meth)acrylate, trimethylolpropane tri(meth)acrylate, pentaerythritol di(meth)acrylate, 3(4),8(9)-bis((meth) acryloyloxymethyl)tricyclo[5.2.1.0$^{2,6}$]decane and dimethacrylates or diacrylates of dihydroxymethyltricyclo[5.2.1.0$^{2,}$ 6]decane. Preferably, all the free-radically polymerizable monomers present in the composition of the invention are selected from the group mentioned.

Particularly preferred in some cases, and therefore present in the composition of the invention, are dimethacrylates or diacrylates of dihydroxymethyltricyclo[5.2.1.0$^{2,6}$]decane, as described, for example, in documents DE 2419887 A1, DE 2406557 A1, DE 2931926 A1, DE 3522005 A1, DE 3522006 A1, DE 3703120 A1, DE 102005021332 A1, DE 102005053775 A1, DE 102006060983 A1, DE 69935794 T2 and DE 102007034457 A1.

Very particularly preferred, and therefore present in the composition of the invention, are free-radically polymerizable monomers selected from the group consisting of 2,2-bis[4-[3-(meth)acryloyloxy2-hydroxypropoxy]phenyl]propane, 2,2-bis[4-(meth)acryloyloxyphenyl]-propane, 2,2-bis[4-(meth)acryloyloxyethoxy-phenyl]propane, 2,2-bis[4-(meth)acryloyloxydiethoxyphenyl]propane, 2,2-bis[4-(meth)acryloyloxytriethoxy-phenyl]-propane, 2,2-bis[4-(meth)acryloyloxytetraethoxyphenyl]propane, 2,2-bis[4-(meth)acryloyloxypen-taethoxyphenyl]propane, 2,2-bis[4-(meth)acryloyloxydipropoxphenyl]propane, 2,2-bis[4-(meth)acryloylox-yethoxyphenyl]-2-[4-(meth)acryloyloxydiethoxphenyl]propane, 2-[4-(meth)acryloyloxydiethoxyphenyl]-2-[4-(meth)acryloyloxytriethoxyphenyl]propane, 2-[4-(meth)acryloyloxdipropoxyphenyl]-2-[4-(meth)acryloyloxytriethoxyphenyl]propane, 2,2-bis[4-(meth)acryloyloxyisopropoxyphenyl]propane, 7,7,9-trimethyl-3,14-dioxa-4,13-dioxo-5,12-diazahexadecane 1,16-dioxydi(meth)acrylate, 7,9,9-trimethyl-3,14-dioxa-4,13-dioxo-5,12-diazahexadecane 1,16-dioxydi(meth)acrylate and 3(4),8(9)-bis((meth)acryloyloxymethyl)tricyclo[5.2.1.0$^{2,6}$]decane.

The expression "total amount (B1) of nonaggregated and nonagglomerated inorganic filler particles having a particle size in the range from 7 to 70 nm" refers to the total amount of all filler particles in the composition of the invention that are nonaggregated, nonagglomerated and inorganic and have a particle size in the range from 7 to 70 nm. There thus exists no further amount of such nonaggregated and nonagglomerated inorganic filler particles having a particle size in the range from 7 to 70 nm in the dental light-curable composition of the invention.

The expression "total amount (B2) of inorganic filler particles having a particle size in the range from 0.12 μm to 10 μm" correspondingly refers to the total amount of all inorganic filler particles having a particle size in the range from 0.12 μm to 10 μm in the composition of the invention. There thus exists no further amount of inorganic filler particles having a particle size in the range from 0.12 μm to 10 μm in the dental light-curable composition of the invention.

The "total amount (B2) of inorganic filler particles having a particle size in the range from 0.12 μm to 10 μm" preferably comprises one, two or more materials selected from the group consisting of barium silicate glasses, barium fluorosilicate glasses, strontium silicate glasses, strontium fluorosilicate glasses, barium aluminum silicate glasses, barium borosilicate glasses, barium fluoroaluminosilicate glasses, fluoroaluminum silicate glasses, ytterbium fluoride, feldspar and amorphous materials based on the oxides or mixed oxides of silicon, aluminum, zirconium and/or titanium. Preferably, all the inorganic filler particles having a particle size in the range from 0.12 μm to 10 μm that are present in the composition of the invention are selected from the group mentioned.

For each of the three total amounts (A), (B1) and (B2) discussed, there is no corresponding further total amount or portion that (taking note in each case of the physical characteristics) has a refractive index outside the respective range specified.

The expression "total amount (C) of photoinitiators" refers to the total amount of all photoinitiators in the composition of the invention. Photoinitiators for light curing of free-radically polymerizable monomers are known to those skilled in the art. Preferred photoinitiators in the total amount (C) are selected from the group consisting of camphorquinone (CQ) and ethyl 4-(dimethylamino)benzoate (DABE). Particular preference is given to compositions of the invention that contain, as photoinitiators, both camphorquinone (CQ) and ethyl 4-(dimethylamino)benzoate (DABE).

Preference is given to a dental light-curable composition of the invention wherein the total amount (A) of free-radically polymerizable monomers, the total amount (B1) of nonaggregated and nonagglomerated inorganic filler particles having a particle size in the range from 7 to 70 nm, the total amount (B2) of inorganic filler particles having a particle size in the range from 0.12 μm to 10 μm, and the total amount (C) of photoinitiators is chosen such that the dental light-curable composition has a depth of cure of 3.5 mm or more on incidence of light from an LED with a radiation flux maximum at a wavelength in the range from 440 to 490 nm, an irradiation time of 10 s and an irradiation intensity of 1000 mW/cm$^2$, and/or (preferably "and")

the dental light-curable composition after curing has a translucence of less than 45%, preferably has a translucence of less than 40%, more preferably has a translucence of less than 35%.

As defined above and in the appended claims, a preferred dental light-curable composition of the invention has a depth of cure (depth of polymerization) of 3.5 mm or more on incidence of light from an LED having a radiation flux maximum at a wavelength in the range from 440 to 490 nm, an irradiation time of 10 s and an irradiation intensity of 1000 mW/cm$^2$. The person skilled in the art is familiar with the determination of depth of cure of dental light-curable compositions. Unless stated otherwise in the individual case, figures associated with the present invention in the present text that are given for depth of cure on incidence of light from an LED having a radiation flux maximum at a wavelength in the range from 440 to 490 nm, an irradiation time of 10 s and an irradiation intensity of 1000 mW/cm$^2$ are based on measurements according to ISO 4049:2019.

As stated above and in the appended claims, a preferred dental light-curable composition of the invention after curing has a translucence of less than 45%, preferably a translucence of less than 40%, more preferably a translucence of less than 35%. Such low translucences are particularly preferred for restorations in the visible anterior region. Translucence measurements are familiar to the person skilled in the art. Unless stated otherwise in the individual case, measurement values given in connection with the present invention are based on measurements by the test method specified below.

Preference is given to a dental light-curable composition of the invention, wherein the following condition applies to the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.020<n_{A,470\ nm}<n_{B1,470\ nm}+0.025,$$

preferably $n_{B1,470\ nm}-0.015<n_{A,470\ nm}<n_{B1,470\ nm}+0.020,$ and/or (preferably "and")

where the following condition applies to the refractive indices of the total amount (A) of free-radically polymerizable monomers and the total amount (B2) of inorganic filler particles having a particle size in the range from 0.12 μm to 10 μm:

$$n_{B2,470\ nm}-0.010<n_{A,470\ nm}<n_{B2,470\ nm}+0.035,$$

preferably $n_{B2,470\ nm}-0.005<n_{A,470\ nm}<n_{B2,470\ nm}+0.030,$ and/or (preferably "and")

where the following condition applies to the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.015<n_{B1,470\ nm}<n_{B2,470\ nm}+0.030,$$

preferably $n_{B2,470\ nm}-0.010<n_{B1,470\ nm}<n_{B2,470\ nm}+0.025.$

According to the above details, it is particularly preferable when the refractive indices (measured at 470 nm, i.e. within the wavelength range of blue light) of the total amount (A) of free-radically polymerizable monomers and of the total amount (B1) of nonaggregated and nonagglomerated inorganic filler particles having a particle size in the range from 7 to 70 nm are particularly close to one another. When blue light is used, this results in particularly high translucence and hence a particularly high depth of cure. Such high depth of cure of dental light-curable compositions are particularly preferable for filling of a cavity in the posterior region. It has been found that the total amount (B1) of nonaggregated and nonagglomerated inorganic filler particles having a particle size in the range from 7 to 70 nm should have a refractive index very substantially identical to the refractive index of the total amount (A) of free-radically polymerizable monomers.

As set out above, it is likewise particularly preferable when the refractive indices of the total amount (A) of free-radically polymerizable monomers and of the total amount (B2) of inorganic filler particles having a particle size in the range from 0.12 μm to 10 μm are particularly close to one another. In this respect too, it has been found that the respective refractive indices should be very substantially identical.

It is likewise particularly preferable when the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm are particularly close to one another. It has also been found here that the respective refractive indices of the nano- and microfiller particles should be very substantially identical.

Preferably, the above-discussed preferred configurations are combined with one another since particularly low translucence after curing and particularly high depth of cure are thus achieved simultaneously.

Preference is given to a dental light-curable composition of the invention (preferably as identified above or hereinafter as preferred), wherein the total amount (A) of free-radically polymerizable monomers is in the range from 21 to 34 percent by volume, based on the overall dental light-curable composition, and/or is in the range from 6 to 20 percent by weight, based on the overall dental light-curable composition, and/or (preferably "and")

the total amount (B1) of nonaggregated and nonagglomerated inorganic filler particles having a particle size in the range from 7 to 70 nm, preferably the total amount (B1-p1) of nonaggregated and nonagglomerated inorganic filler particles having a particle size in the range from 7 to 60 nm, more preferably the total amount (B1-p2) of nonaggregated and nonagglomerated inorganic filler particles having a particle size in the range from 7 to 50 nm, is in the range from 13 to 27 percent by volume, preferably in the range from 15 to 25 percent by volume, based on the overall dental light-curable composition, and/or is in the range from 10 to 66 percent by weight, preferably in the range from 13 to 63 percent by weight, more preferably in the range from 14 to 60 percent by weight, based on the overall dental light-curable composition, and/or (preferably "and")

the total amount (B2) of inorganic filler particles having a particle size in the range from 0.12 μm to 10 μm, preferably the total amount (B2-p1) of inorganic filler particles having a particle size in the range from 0.18 μm to 10 μm, more preferably the total amount (B2-p2) of inorganic filler particles having a particle size in the range from 0.40 μm to 10 μm, is in the range from 42 to 60 percent by volume, based on the overall dental light-curable composition, and/or is in the range from 28 to 70 percent by weight, based on the overall dental light-curable composition.

Preference is given to configurations in which said total amounts (A), (B1) and (B2) collectively make up by far the predominant proportion of the dental light-curable composition of the invention.

Preferably, the total amounts (A), (B1) and (B2) of a dental light-curable composition of the invention (preferably of a dental light-curable composition of the invention as identified above as preferred) add up to at least 95 percent by volume, preferably at least 98 percent by volume, based on the overall dental light-curable composition (i.e. the total volume thereof), and/or to at least 95 percent by weight, preferably 98 percent by weight, based on the overall dental light-curable composition (i.e. the total mass thereof).

Also preferably, a dental light-curable composition of the invention (preferably as identified above or hereinafter as preferred) contains an amount of less than 5 percent by weight, preferably of less than 3 percent by weight, of composite fillers, in each case based on the overall dental light-curable composition (i.e. the total mass thereof).

The term "composite fillers" designates organic polymer particles, which for their part are filled with inorganic fillers or inorganic filler particles respectively. This corresponds to the definition of WO 2021/148667 A1 regarding "Kompositfüllstoffe".

Particularly preferred is a dental light-curable composition of the invention (preferably as identified above or hereinafter as preferred) that does not contain any composite fillers.

According to the above details, it is particularly preferred that dental light-curable compositions of the invention contain a high proportion of volume and/or proportion of mass of total amounts (A), (B1) and (B2) (as described above). Surprisingly, it has been shown that dental light-curable compositions of the invention can do without composite fillers, which are commonly used in large quantities in the prior art, see e.g. the dental materials according to WO 2021/148667 A1 and EP 3 854 374 A1 with a proportion of composite fillers of up to 60 percent of weight. In particular, the specific adjustment of the respective proportions of volume and/or proportions of mass of total amounts (A), (B1) and (B2) leads to excellent mechanical properties such as modulus of elasticity, ACTA abrasion and polymerization shrinkage of the cured dental composites (as described hereinabove and hereinafter) even in the absence of composite fillers.

In relation to mechanical properties such as modulus of elasticity, ACTA abrasion and polymerization shrinkage of the cured dental composites, it is particularly advantageous when the preferred dental light-curable compositions of the invention have a comparatively high proportion of nanofiller particles in the total amount (B1) of at least 13 and preferably at least 15 percent by volume, based on the overall dental light-curable composition.

According to the invention, there is an upper limit to the proportion by volume of nanofiller particles in the total amount (B1) since the dental light-curable compositions can frequently be processed only with particular difficulty when the solids content is too high.

Preferred is a dental light-curable composition of the invention (preferably as identified above or hereinafter as preferred), wherein the total amount (B1) of nonaggregated and nonagglomerated inorganic filler particles having a particle size in the range from 7 to 70 nm, preferably the total amount (B1-p1) of nonaggregated and nonagglomerated inorganic filler particles having a particle size in the range from 7 to 60 nm, more preferably the total amount (B1-p2) of nonaggregated and nonagglomerated inorganic filler particles having a particle size in the range from 7 to 50 nm, accounts for an amount of more than 31 percent by weight, in each case based on the overall dental light-curable composition (i.e. the total mass thereof).

According to the invention, there is an upper limit to the proportion by mass of nanofiller particles in the total amount (B1) since the dental light-curable compositions can be processed frequently only with particular difficulty when the solids content is too high.

The person skilled in the art, in the selection of the proportion by volume and/or the proportion by mass of the total amount (B1), takes account both of the desired advantageous profile of mechanical properties of the cured dental composites and of the flowability of the dental light-curable composition required for the production of a visible restoration in the anterior region or for filling of a cavity in the posterior region.

Corresponding considerations are applicable to the total amount (B2); in this respect, a proportion of the total amount (B2) of at least 42 percent by volume, based on the overall dental light-curable composition, is particularly advantageous for achievement of advantageous mechanical properties of the cured dental composite.

The reason for the difference between the preferred percentage by volume ranges and percentage by weight ranges for the total amount (B1) is the material-specific densities of the inorganic filler particles. For instance, the density of ytterbium fluoride at 8.2 g/cm$^3$ is about four times higher than that of $SiO_2$ at 2.2 g/cm$^3$. What is crucial for the advantageous mechanical properties here is the percentage by volume of nanofiller particles for the total amount (B1).

Preference is given to a dental light-curable composition of the invention (preferably as identified above or hereinafter as preferred), wherein the total amount (B1) of nonaggregated and nonagglomerated inorganic filler particles having a particle size in the range from 7 to 70 nm consists of filler particles which (i) have an identical or different physical composition and (ii) have additionally been surface-modified or have not been surface-modified, wherein the filler particles preferably (i) have an identical physical composition and (ii) have additionally been surface-modified.

In this case, the total amount (B1) preferably consists of an amount of filler particles of the same physical composition that have a refractive index $n_{B1,\ 470\ nm}$ in the range from 1.460 to 1.570, where the filler particles in this amount have additionally been surface-modified or have not been surface-modified, or of a mixture of two, three or more than three portions of filler particles, where the filler particles within each portion (i) have an identical physical composition and (ii) have additionally been surface-modified or have not been surface-modified, but the filler particles from different portions have a different physical composition, where each of these portions on its own has a refractive index $n_{B1,\ 470\ nm}$ in the range from 1.460 to 1.570, where the difference between the highest refractive index and the lowest refractive index of each of the portions considered on its own is preferably less than 0.01.

For the above definition of preferred filler particles in the total amount (B1), a distinction is made between the (i) physical composition of the filler particles without taking account of any surface modification, and (ii) any additional surface modification. For instance, first and second filler particles within the total amount (B1) may have an identical physical composition, where the first filler particles have additionally been surface-modified and the second filler particles (given the same physical composition) have not been surface-modified. Moreover, there may, for example, be filler particles in the total amount (B1) that have a different physical composition but have been surface-modified in each case.

Surface modifications present here may be the same or different.

Preferably, however—as set out above—the filler particles in the total amount (B1) have an identical physical composition and have additionally been surface-modified (in the same or a different manner).

Particularly preferred nonaggregated and nonagglomerated inorganic filler particles having a particle size in the range from 7 to 70 nm comprise or consist of ytterbium trifluoride ($YbF_3$) or silicon dioxide ($SiO_2$). In this case, the preferred particles of ytterbium trifluoride ($YbF_3$) have preferably been surface-modified, more preferably surface-modified with MDP. MDP here means 10-[(2-methylprop-2-enoyl)oxy]decyl dihydrogenphosphate (CAS No. 85590-00-7). The preferred filler particles of silicon dioxide ($SiO_2$) have preferably been surface-modified, preferably surface-modified with MPS, where MPS means [3-(methacryloyloxy)propyl]trimethoxysilane (CAS No. 2530-85-0). The aforementioned "physical composition" is thus characterized by "ytterbium trifluoride" or "silicon dioxide"; the surface modification is characterized by specification of the chemical compound used for surface modification of the respective inorganic material. Corresponding preferred filler particles may also be used in combination with one another.

Preference is given to a dental light-curable composition of the invention (preferably as identified above or hereinafter as preferred) wherein the total amount (B2-p2) of inorganic filler particles having a particle size in the range from 0.40 μm to 10 μm, preferably the total amount (B2-p1) of inorganic filler particles having a particle size in the range from 0.18 μm to 10 μm, more preferably the total amount (B2) of inorganic filler particles having a particle size in the range from 0.12 μm to 10 μm, consists of an amount of filler particles of the same physical composition that has preferably additionally been surface-modified, where this amount of filler particles has a refractive index $n_{B2,\ 470\ nm}$ in the range from 1.450 to 1.560, or consists of a mixture of two, three or more than three portions of filler particles, where the filler particles within each portion have an identical physical composition and have preferably additionally been surface-modified, but the filler particles from different portions have a different physical composition, where each of these portions on its own has a refractive index $n_{B2,\ 470\ nm}$ in the range from 1.450 to 1.560, where the difference between the highest refractive index and the lowest refractive index of each of the portions considered on its own is preferably less than 0.01.

The details with regard to the terms "physical composition" and "surface-modified" that are given in connection with preferred configurations of the inorganic filler particles in the total amount (B1) are correspondingly applicable to the total amount (B2).

In in-house experiments, it has been found that, when a mixture of two, three or more than three portions of filler particles is used, it should be ensured that the refractive index of each individual portion, preferably on its own, has the properties specified for the total amount (B2), and that the difference of the refractive indices of the portions is at a minimum. In this way, particularly high translucence of the uncured composition and hence a particularly high depth of cure is attained.

Preference is given to a dental light-curable composition of the invention (preferably as identified above or hereinafter as preferred) wherein the total amount (A) of free-radically polymerizable monomers is selected such that a polymeric material is obtainable by light-curing thereof that has a refractive index increased by at least 0.015, preferably at least 0.020, determined at a wavelength of 589 nm.

The wavelength of 589 nm mentioned here is within the range of yellow light. This is the wavelength of the sodium D line which is known to the person skilled in the art. What are thus compared are the refractive index of the total amount (A) of free-radically polymerizable monomers before curing and after curing of the dental light-curable composition, with measurement in each case using light of wavelength 589 nm. This wavelength is within the green-yellow region of the light spectrum (500 nm-600 nm) which is perceived with particular intensity by the human eye and is thus relevant in the assessment of a visible restoration in the anterior region and makes a crucial contribution to the overall aesthetic impression. The invention takes account of the fact that the refractive index of the total amount (A) of free-radically polymerizable monomers prior to curing is much smaller than the refractive index of the resulting polymeric material. The change in this refractive index (determined at a wavelength of 589 nm) is crucial for the cured dental material to appear opaque (i.e. less translucent) to the observer, even though the dental light-curable composition of the invention had particularly high translucence prior to curing. Elevated opacity (reduced translucence) after light curing is achieved because an increase in refractive index (proceeding from the monomers to the polymer) takes place without simultaneous variation in the refractive indices of the fillers (since the filler particles do not of course undergo any physical change on light curing of the monomers).

After light curing, the result is a difference in refractive index between the cured polymer on the one hand and the filler particles embedded therein on the other hand. This difference in refractive index is responsible in a manner known per se for the elevated opacity (reduced translucence).

Preference is given to a dental light-curable composition of the invention (preferably as identified above or hereinafter as preferred), comprising, in addition to the total amounts (A), (B1), (B2) and (C), a total amount (D) of colorants selected from the group consisting of inorganic color pigments, organic color pigments and dyes.

The colorants in the total amount (D) are preferably selected from the group consisting of iron oxide, titanium dioxide, barium sulfate and aluminum oxide.

Preference is given to such a dental light-curable composition of the invention which thus additionally comprises a total amount (D) of colorants, wherein the following condition applies to the translucence $T_{Col}$ of this dental light-curable composition after curing compared to the translucence $T_{NoCol}$ of a dental light-curable composition of otherwise identical composition that does not comprise any additional colorants:

$$35\% > T_{NoCol} - T_{Col} > 5\%,\ \text{preferably}\ 30\% > T_{NoCol} - T_{Col} > 5\%,\ \text{more preferably}\ 25\% > T_{NoCol} - T_{Col} > 5\%,$$

and/or (preferably "and")

wherein the total amount (D) of the one or more colorants forms a proportion by volume of not more than 800 ppm, preferably not more than 600 ppm, more preferably not more than 400 ppm, based on the overall dental light-curable composition, and/or forms a proportion by mass of not more than 2000 ppm, preferably not more than 1500 ppm, more preferably not more than 1000 ppm, based on the overall dental light-curable composition, and/or (preferably "and")

wherein the dental light-curable composition after curing has a translucence $T_{Col}$ of less than 28%, preferably of less than 26%, more preferably of less than 24%, especially preferably of less than 22%.

The translucence $T_{NoCol}$ of the dental light-curable composition which is otherwise of identical composition and comprises no additional colorants is higher than the translucence $T_{Col}$ of the preferred dental light-curable composition that comprises a total amount (D) of colorants. The difference between the two translucences mentioned is preferably greater than 5%. Translucence is determined after curing in each case, and so it becomes clear that the addition of colorants makes a preferred contribution to the overall aesthetic impression, for example of dental restorations in the visible anterior region, by reducing the translucence in the desired manner. But the reduction in translucence should on the other hand also not be excessively great, since the result would likewise not be an aesthetic impression corresponding to a natural tooth. The effect achieved with regard to the reduction in translucence through the addition of colorants in a total amount (D) is additive with the effects discussed further up that are based on the change in refractive index of the polymer material (the free-radically polymerizable monomers in the total amount (A) react via light curing to give a cured polymer having elevated refractive index).

As set out above, the proportion of the additional colorants in the total amount (D) in the dental light-curable composition of the invention is preferably small (see the above details of preferred maximum proportions by volume and preferred maximum proportions by mass).

It is a particular advantage of the present invention that, even when small amounts of colorants are used, a desired low translucence of the dental light-curable composition is achieved after curing. This is of course because of the already above-discussed effect of the increase in refractive index of the polymer material resulting from the polymerization of the monomers used. The effect of the small proportion of colorants which is required to achieve the required translucence after curing is that the depth of cure (prior to curing) of the dental light-curable composition of the invention remains particularly high even in the presence of colorants, by contrast with compositions from the prior art.

After curing, a preferred dental light-curable composition of the invention that contains additional colorants has a translucence $T_{Col}$ of less than 28%, preferably of less than 26%, more preferably of less than 24%, especially preferably of less than 22%.

Preference is given to a dental light-curable composition of the invention (preferably as identified above or hereinafter as preferred), wherein the total amount of all inorganic particles having a particle size of not more than 0.12 μm in the composition has an average volume-based particle size of less than 70 nm, determined by means of dynamic light scattering, preferably an average volume-based particle size of less than 66 nm.

In the prior art, inorganic nanoparticles having an average particle size of less than 70 nm were considered to be disadvantageous. For example, EP 2 902 007 A1 thus teaches that inorganic fillers used should have an average particle size of not less than 0.07 μm.

In the context of the present invention, however, the use of such particularly small particle sizes is particularly preferred. What is important here, however, is that the refractive indices of the materials used are selected as defined above.

Preference is given to a dental light-curable composition of the invention (preferably as identified above or hereinafter as preferred), wherein the following conditions apply to the color values of the dental light-curable composition after curing, determined according to EN ISO 11664-4:

$$55.0<L^*<80.0, \text{ preferably } 64.0<L^*<75.0, \text{ and}$$

$$-1.5<a^*<4.5, \text{ preferably } 2.0<a^*<4.5, \text{ and}$$

$$5.0<b^*<20.0, \text{ preferably } 13.0<b^*<20.0,$$

preferably:

$$64.0<L^*<75.0, \text{ and}$$

$$2.0<a^*<4.5, \text{ and}$$

$$13.0<b^*<20.0.$$

The color of the dental light-curable composition may be adjusted here via appropriate use of suitable colorants. The above-specified preferred color values of the dental light-curable composition after curing correspond to the color of typical natural tooth substances.

Preference is given to a dental light-curable composition of the invention (preferably as identified above or hereinafter as preferred), comprising, in addition to the total amounts (A), (B1), (B2) and (C), a total amount (E) of one, two, three or more than three auxiliaries that are not colorants, where the auxiliaries in the total amount (E) are selected from the group consisting of:

- rheological auxiliaries,
- polymerization initiators that are not photoinitiators,
- chemical compounds as catalysts or constituents of catalyst systems,
- stabilizers, especially UV and daylight stabilizers,
- inhibitors,
- activators,
- molecular weight regulators,
- preservatives,
- interface-active substances,
- biocides, preferably bactericides,
- organic polymers and oligomers and compounds having high molecular weights, preferably plasticizers,
- thickeners, and
- dental medicaments.

Preferred dental light-curable compositions of the invention (as defined above, preferably as defined above as preferred) preferably contain one or more inhibitors (also called stabilizers). These are typically added in order to avoid spontaneous polymerization. This increases the storage stability of the preferred dental light-curable compositions. Inhibitors for use with preference are phenol derivatives such as hydroquinone monomethyl ether (MeHQ) or 2,6-di-tert-butyl-4-methylphenol (BHT). Further inhibitors for use with preference, such as tert-butylhydroxyanisole (BHA), 2,2-diphenyl-1-picrylhydrazyl, galvinoxyl, triphenylmethyl radicals, 2,2,6,6-tetramethylpiperidinyl-1-oxyl radicals (TEMPO) and derivatives of TEMPO or phenothiazine and derivatives of that compound, are described in EP 0 783 880 B1. Alternative preferred inhibitors are specified in DE 101 19 831 A1 and in EP 1 563 821 A1.

Molecular weight regulators used with preference are, for example, aldehydes and ketones, such as formaldehyde, acetaldehyde, propionaldehyde, n-butyraldehyde, isobutyraldehyde, methyl ethyl ketone, acetone, methyl isobutyl ketone, formic acid, ammonium formate, hydroxylammonium sulfate and hydroxylammonium phosphate, compounds containing sulfur in organically bound form, such as di-n-butyl sulfide, di-n-octyl sulfide, diphenyl sulfide, diisopropyl disulfide, di-n-butyl disulfide, di-n-hexyl disulfide, diacetyl disulfide and di-tert-butyl trisulfide, compounds containing sulfur in the form of SH groups, such as n-butyl mercaptan, n-hexyl mercaptan and n-dodecyl mercaptan, octadecyl mercaptan, further sulfur compounds such as hydrogensulfites, disulfites, compounds such as mercaptoethanol, mercaptobutanol, mercaptoacetic acid, 3-mercaptopropionic acid, mercaptosuccinic acid, thioglycerol, thioglycolic acid, diethanol sulfide, thiodiglycol, ethylthioethanol, 2,2,4,6,6-pentamethylheptane-4-thiol, 2,2,4,6,6,8,8-heptamethylnonane-4-thiol, thiourea, dimethyl sulfoxide, ethylhexyl thioglycolate, pentaerythritol tetrathioglycolate, mercap-topropyltrimethoxysilane, then allyl compounds such as allyl alcohol, allyl bromide, or benzyl compounds such as benzyl chloride or alkyl halides such as chloroform, bromotrichloromethane or tetrachloromethane, tetrabromomethane, methylene chloride, and additionally lower and higher molecular weight monohydric or polyhydric alcohols such as methanol, ethanol, n-propanol, isopropanol, tert-butanol, sec-butanol, n-butanol, amyl alcohol, cyclohexanol, octanol, dodecanol, 1-ethylhexanol, glycerol, stearyl alcohol, oleyl alcohol, hydroxyethyl methacrylate or amines such as triethylamine, and toluene or ethylbenzene.

Further, and in many cases preferred, molecular weight regulators are, for example, various terpenes, especially terpinenes (α-terpinene,β-terpinene, γ-terpinene), phellandrenes (α-phellandrene,β-phellandrene) and terpineols (also called δ-terpines), 1,4-cyclohexadiene (optionally substituted), 1,3-cyclohexadiene (optionally substituted), 1,4-dihydronaphthalene, 1,4,5,8-tetrahydronaphthalene, 2,5-dihydrofuran or dimeric α-styrene (2,4-diphenyl-4-methyl-1-pentene), and also linoleic acid and α-linolenic acid.

The present invention also relates to a dental restoration and to a cured dental material. The invention includes a dental restoration or a cured dental material, preferably a visible dental restoration in the anterior region or a filling of a cavity in the posterior region, obtainable by light curing of a dental light-curable composition of the invention (preferably as identified above as preferred), preferably using light within a wave-length range from 450 nm to 490 nm.

The above details relating to preferred dental light-curable compositions of the invention are correspondingly applicable here in full. As already set out, it is advantageous here to combine features of preferred configurations of a dental light-curable composition of the invention with one another.

The invention also relates to a method of producing a dental light-curable composition (preferably of the invention, preferably as identified above as preferred), comprising the following steps:

(i) selecting a total amount (A) of free-radically polymerizable monomers, a total amount (B1) of nonaggregated and nonagglomerated inorganic filler particles having a particle size in the range from 7 to 70 nm, a total amount (B2) of inorganic filler particles having a particle size in the range from 0.12 μm to 10 μm, and a total amount (C) of photoinitiators, with the following applicable criteria relating to the selection of the total amounts (A), (B1) and (B2), i.e. observation and implementation of these by the person skilled in the art when performing the method:

the total amount (A) of free-radically polymerizable monomers has a refractive index $n_{A,\ 470\ nm}$ in the range from 1.470 to 1.560, the total amount (B1) of nonaggregated and nonagglomerated inorganic filler particles having a particle size in the range from 7 to 70 nm has a refractive index $n_{B1,\ 470\ nm}$ in the range from 1.460 to 1.570, the total amount (B2) of inorganic filler particles having a particle size in the range from 0.12 μm to 10 μm has a refractive index $n_{B2,\ 470\ nm}$ in the range from 1.450 to 1.560, for the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.025<n_{A,470\ nm}<n_{B1,470\ nm}+0.030,$$

for the refractive indices of the total amount (A) of free-radically polymerizable monomers and the total amount (B2) of inorganic filler particles having a particle size in the range from 0.12 μm to 10 μm:

$$n_{B2,470\ nm}-0.015<n_{A,470\ nm}<n_{B2,470\ nm}+0.040,$$

for the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.020<n_{B1,470\ nm}<n_{B2,470\ nm}+0.035,$$

(ii) producing or providing the selected total amounts (A), (B1), (B2) and (C), (iii) mixing the total amounts (A), (B1), (B2) and (C) produced or provided in step (ii) and optionally additionally a total amount (D) of colorants and/or a total amount (E) of one, two, three or more than three additional auxiliaries, so as to result in the dental light-curable composition.

It will be apparent that every individual total amount and substance used in the method of the invention may in itself already be known from the prior art. But it is a particular achievement of the present invention that said substances and the total amounts thereof are selected and adjusted so as to result in a dental light-curable composition suitable both for production of a visible restoration in the anterior region and for filling of a cavity in the posterior region. In the case of suitable selection, the result is namely a dental light-curable composition of the invention with the excellent properties already mentioned above, namely high depth of cure, preferably a depth of cure of 3.5 mm or more, on irradiation with light from an LED with a radiation flux maximum at a wavelength in the range from 440 to 490 nm, an irradiation time of 10 s and an irradiation intensity of 1000 $mW/cm^2$, and simultaneously having low translucence after curing, preferably a translucence of less than 45%.

It is a particular achievement here by the inventors of the present invention that the selection is made on the basis of refractive indices that have been determined at a wavelength of 470 nm, i.e. using a specific blue light as also used for curing in dental practice.

The invention also relates to the use of one, two or all (preferably all) of the following total amounts:

total amount (A) of free-radically polymerizable monomers, where this total amount (A) consists of one, two, three or more than three free-radically polymerizable monomers and has a refractive index $n_{A,\ 470\ nm}$ in the range from 1.470 to 1.560, total amount (B1) of nonaggregated and nonagglomerated inorganic filler particles having a particle size in the range from 7 to 70 nm, where this total amount (B1) has a refractive index $n_{B1,\ 470\ nm}$ in the range from 1.460 to 1.570, total amount (B2) of inorganic filler particles having a particle size in the range from 0.12 μm to 10 μm, where this total amount (B2) has a refractive index $n_{B2,\ 470\ nm}$ in the range from 1.450 to 1.560, for production of a dental light-curable composition (preferably of a dental light-curable composition of the invention as defined above and preferably as identified above as preferred) suitable for elective production of a visible restoration in the anterior region or for filling of a cavity in the posterior region, wherein the dental light-curable composition has a depth of cure of 3.5 mm or more on incidence of light from an LED with a radiation flux maximum at a wavelength in the range from 440 to 490 nm, an irradiation time of 10 s and an irradiation intensity of 1000 $mW/cm^2$, and/or (preferably "and")

after curing has a translucence of less than 45%.

Both for the method of the invention for production of a dental light-curable composition and for the inventive use of one, two or all of the total amounts specified, it is of course the case that the preferred configurations specified in connection with the dental light-curable composition of the invention are correspondingly applicable; it is again the case that combinations of features of such preferred configurations are likewise preferred.

The invention also relates to a dental light-curable composition of the invention for use in a method of surgical or therapeutic treatment of the human or animal body and/or for use in a diagnostic method performed on the human or animal body, preferably for specific use in a therapeutic method for temporary or permanent visible restoration in the anterior region or in a therapeutic method for temporary or permanent filling of a cavity in the posterior region, or in a therapeutic method as tooth filling material, dental cement, dental lining material, as free-flowing composite material (flow material), as crown material, as inlay, as onlay, as bridge material and/or as core buildup material.

The invention of course also relates to the corresponding specific methods themselves. The above remarks relating to preferred configurations of dental light-curable compositions of the invention etc. are also applicable here correspondingly.

The present invention thus also relates to a method of producing a visible restoration in the anterior region or for filling of a cavity in the posterior region, comprising the following steps:

(i) producing or providing a dental light-curable composition of the invention (preferably as identified above as preferred), (ii) applying the dental light-curable composition produced or provided to the part of the teeth to be restored or filled, (iii) curing the dental light-curable composition applied by irradiating with light in the wavelength range from 450 nm to 490 nm.

In this respect too, the above elucidations relating to preferred dental light-curable compositions of the invention are applicable of course.

The invention is elucidated in detail hereinafter by examples:

EXAMPLES

I. Methods of Determination:

I.1 The particle size distribution of the nanoscale fillers in the total amount (B1) was determined by means of dynamic light scattering using a Malvern ZetaSizer Nano ZS. For this purpose, the nanoparticles to be analyzed were finely dispersed in a suitable solvent with the aid of ultrasound and then analyzed at a wavelength of 633 nm. The data obtained for the volume-weighted particle size distribution were evaluated and displayed using the ZetaSizer software V7.13. The reported particle sizes are the d50 values in volume-weighted evaluation.

I.2 The particle size distribution of the microscale fillers in the total amount (B2) was determined by means of static light scatter on a Beckman Coulter LS 13 320. The reported particle sizes are the d50 values in volume-weighted evaluation.

I.3 Translucence was determined on produced specimens of cured dental material by introducing the dental light-curable composition into an annular metal mold having an internal diameter of 12 mm and a thickness of 2 mm, covering it with a polyester film at the top and bottom, and pressing, light-curing and then demolding, with analysis of the specimens of cured dental material thus produced using a Hunterlab ColorFlex EZ 45/0 twin-beam spectrophotometer using D65 standard illuminant and at a 10° observer angle in reflection mode against a black tile and a white tile, in order to determine the tristimulus values $Y_{black}$ and $Y_{white}$ from the measurement against the black and white tile respectively. Translucence was determined here in percent by the following formula:

$$\text{Translucence [\%]}=100-100\cdot Y_{black}/Y_{white}$$

I.4 Color was determined on produced specimens of cured dental material by introducing the dental light-curable composition into an annular metal mold having an internal diameter of 12 mm and a thickness of 2 mm, covering it with a polyester film at the top and bottom, and pressing, light-curing and then demolding, with analysis of the specimens of cured dental material thus produced using a Hunterlab ColorFlex EZ 45/0 twin-beam spectrophotometer using D65 standard illuminant and at a 10° observer angle in reflection mode against a black tile and a white tile. The L*a*b* values come from the measurement against the white tile.

I.5 The refractive indices of the total amount (A) of free-radically polymerizable monomers were measured at 20° C. with an automatic Schmidt+Haensch ATR-L dispersion refractometer and noted for the wavelengths of 470 nm (blue) and 589 nm (yellow sodium D line).

I.6 The refractive indices of the sols (colloidal solution of nonaggregated and nonagglomerated inorganic filler particles having a particle size in the range from 7 to 70 nm from the total amount (B) in the total amount (A) of free-radically polymerizable monomers) were measured at 20° C. with an automatic Schmidt+Haensch ATR-L dispersion refractometer and noted for the wavelengths of 470 nm (blue) and 589 nm (yellow sodium D line). Using the equation $n_{Sol}=x_{B1}\times n_{B1}+x_A\times n_A$ with the refractive indices n and the percentages by volume x, a reverse calculation was made of the refractive index $n_{B1}$ of the total amount (B1) of non-aggregated and nonagglomerated inorganic filler particles having a particle size in the range from 7 to 70 nm (nanoparticles).

I.7 The refractive indices for the wavelengths of 470 nm (blue) and 589 nm (yellow sodium D line) in the total amount (B2) of inorganic filler particles having a particle size in the range from 0.12 μm to 10 μm (microparticles) were determined by the immersion method. The microparticles were dispersed at 20° C. in liquids having different refractive indices (called immersion liquids). The greater the difference in refractive index between liquid and microparticles, the greater the clarity of the contours of the microparticles. If the refractive index of the liquid is then changed such that it approaches that of the microparticles, the particle contours become weaker and disappear completely when the refractive indices are matched. Suitable immersion liquids are liquids having known refractive index, for example mixtures of benzyl salicylate (nD20=1.536) and triacetin (nD20=1.431) or bromonaphthalene (nD20=1.657). By varying the ratios of the amounts of these substances, it is possible to match the refractive index of the mixture to that of the microparticle to be analyzed. In the case of agreement of the refractive indices, the refractive index of the immersion liquid is determined with a refractometer as described above. The agreement of the refractive indices of microparticles and immersion liquid can be ascertained by observing the Becke line (Becke line method). This is a bright band of light which is manifested on defocusing of an interface. The microparticle to be examined is introduced into a liquid having known refractive index and observed under a microscope with monochromatic light of the appropriate wavelengths of 470 nm (blue) and 589 nm (yellow sodium D line). If particle and liquid have different refractive indices, a narrow bright ring (Becke line) is observed around each particle, which moves on focusing. This operation is repeated in various liquids having different refractive indices until no Becke lines occur any longer, and hence the refractive indices of particle and liquid correspond.

I.8 Depth of cure (DOC) (=depth of polymerization) was ascertained by the method described in ISO 4049:2019 under "depth of cure" (depth of polymerization) using a Celalux 2 light curing device (VOCO GmbH, Cuxhaven). The measurements were conducted on incidence of light from the LED from the Celalux light curing device with a radiation flux maximum at a wavelength in the range from 440 to 490 nm, an irradiation time of 10 s or 20 s and an irradiation intensity of 1000 mW/cm$^2$.

I.9 Modulus of elasticity (E modulus) was determined from a stress-strain diagram from a flexural strength measurement using the slope in the linear elastic region of the graph. Flexural strength was determined by production and curing of test specimens having dimensions of 2×2×25 mm analogously to the method described in ISO 4049:2019. The measurement, in which the test specimens are subjected to load in a three-point bending test until they fracture, was effected using a universal tester in accordance with the provisions from the standard, as was the evaluation.

I.10 ACTA abrasion was determined after curing by means of a wear simulation. The wear simulation was effected with a TMA 1 three-media abrasion machine (SD-Mechatronik, 83620 Feldkirchen-Westerham) according to de Gee (de Gee, A. J.; Pallav, P.; Occlusal wear simulation with the ACTA wear machine; J. Dent.; 1994; 22; Suppl. 1; p. 21-27) and ISO/TS 14569-2. The evaluation was effected with a TMAM LS laser scanner (SD-Mechatronik, Feldkirchen-Westerham).

I.11 Polymerization shrinkage was ascertained by the bonded disk method (Watts, D. C.; Cash, A. J.; Determination of polymerization shrinkage kinetics in visible-light-cured materials: methods development; Dent. Mater.; 1991; 7; 281). The test specimens were exposed with the Celalux 2 light curing device (VOCO GmbH, Cuxhaven) at 23° C. for 40 s. Shrinkage was read off after one hour.

II. Materials Used:

The materials used in the examples are listed in table 1. The materials used are merely illustrative. It is also possible to use other materials and combinations of materials, provided that they have properties as must exist in dental light-curable compositions of the invention; for the corresponding properties of the respective materials see the above description and the claims.

The listing in table 1 gives the chemical designation, the abbreviations used hereinafter, and the trade name and CAS number (CAS no.) of the materials used. In addition, the materials in column 5 of table 1 ("example of") are assigned to the defined total amounts (A), (B1), (B2), (C), (D) and (E) according to the above description and claims that follow.

In table 1, the following have the following meanings:

(1): free-radically polymerizable monomer in the total amount (A), where this total amount consists of one, two, three or more than three free-radically polymerizable monomers and has a refractive index $n_{A,\ 470\ nm}$ in the range from 1.470 to 1.560

(2): nonaggregated and nonagglomerated inorganic filler particles in the total amount (B1) having a particle size in the range from 7 to 70 nm, where this total amount has a refractive index $n_{B1,\ 470\ nm}$ in the range from 1.460 to 1.570

(3): surface modifiers of the filler particles in the total amount (B1)

(4): inorganic filler particles in the total amount (B2) having a particle size in the range from 0.12 μm to 10 μm, where this total amount has a refractive index $n_{B2,\ 470\ nm}$ in the range from 1.450 to 1.560

(5): color pigments in the total amount (D) of colorants (6): photoinitiators in the total amount (C)

(7): auxiliaries in the total amount (E)

TABLE 1

| Name | Abbreviation | Trade name | CAS no. | Example of |
|---|---|---|---|---|
| Bisphenol A glycidyl dimethacrylate | Bis-GMA | CN151 | 1565-94-2 | (1) |
| Tricyclodecanedimethanol dimethacrylate | TCD-DMA | SR 834 | 43048-08-4 | (1) |

TABLE 1-continued

| Name | Abbreviation | Trade name | CAS no. | Example of |
|---|---|---|---|---|
| Ethoxylated bisphenol A dimethacrylate | Bis-EMA | Miramer M245 | 41637-38-1 | (1) |
| Urethane dimethacrylate | UDMA | HEMA-TMDI | 72869-86-4 | (1) |
| 2,2'-Ethylenedioxydiethyl dimethacrylate | TEDMA | SR 205 | 109-16-0 | (1) |
| Ytterbium trifluoride nanoparticles, 50 nm | — | — | 13760-80-0 | (2) |
| Ytterbium trifluoride nanoparticles, 20 nm | — | — | 13760-80-0 | (2) |
| Ytterbium trifluoride nanoparticles, 15 nm | — | — | 13760-80-0 | (2) |
| Silicon dioxide nanoparticles, 50 nm | — | — | 7631-86-9 | (2) |
| Ytterbium trifluoride nanoparticles having an MDP surface coating, 50 nm | 50 nm $YbF_3$ + MDP | — | — | (2) |
| Ytterbium trifluoride nanoparticles having an MDP surface coating, 20 nm | 20 nm $YbF_3$ + MDP | — | — | (2) |
| Ytterbium trifluoride nanoparticles having an MDP surface coating, 15 nm | 15 nm $YbF_3$ + MDP | — | — | (2) |
| Silicon dioxide nanoparticles having an MPS surface coating, 50 nm | 50 nm $SiO_2$ + MPS | — | — | (2) |
| 10-Methacryloyloxydecyl dihydrogenphosphate | MDP | — | 85590-00-7 | (3) |
| Methacryloyloxypropyltri-methoxysilane | MPS | A 174 | 2530-85-0 | (3) |
| Barium aluminum borosilicate glass, 0.7 μm | Glass ceramic 0.7 μm | GM27884 UF0.7 sil | 65997-17-3 | (4) |
| Barium aluminum borosilicate glass, 2.0 μm | Glass ceramic 2.0 μm | GM27884 UF2.0 sil | 65997-17-3 | (4) |
| Quartz glass 0.7 μm | — | G018-066 | | (4) |
| Iron oxide yellow | FS yellow | C.I. Pigment Yellow 42 | 51274-00-1 | (5) |
| Iron oxide red | FS red | C.I. Pigment Red 101 | 1309-37-1 | (5) |
| Iron oxide black | FS black | C.I. Pigment Black 11 | 1317-61-9 | (5) |
| Titanium dioxide | FS white | C.I. Pigment White 6 | 13463-67-7 | (5) |
| Camphorquinone | CQ | DL-Bornane-2,3-dione | 10373-78-1 | (6) |
| Ethyl 4-dimethylaminobenzoate | DABE | Irgacure EDB | 10287-53-3 | (6) |
| 3,5-Di-tert-butyl-4-hydroxytoluene (polymerization inhibitor) | BHT | Topanol | 128-37-0 | (7) |
| 2-(2H-Benzotriazol-2-yl)-4-methylphenol (UV stabilizer) | BZT | Drometrizole | 2440-22-4 | (7) |

III. Production of Dental Light-Curable Compositions (Examples 1-15):

In a first step, for the production of the individual dental light-curable compositions (examples 1-15), the respective free-radically polymerizable monomers were dissolved in one another with stirring. This resulted in a respective total amount (A) of free-radically polymerizable monomers, the refractive index $n_{A,\ 470\ nm}$ or $n_{A,\ 589\ nm}$ of which was subsequently determined (cf. the test method for determination of the refractive indices).

In a second step, the respective total amount (B1) of nonaggregated and nonagglomerated inorganic filler particles having a particle size in the range from 7 to 70 nm (the ytterbium trifluoride or silicon dioxide nanoparticles in the form of a colloidal solution in alcohol) were weighed into a flask together with the total amount (A) produced in the first step, and the resulting mixture was homogenized by stirring and freed of the solvent on a rotary evaporator. Subsequently, the refractive index of the sol, i.e. of the colloidal solution of nonaggregated and nonagglomerated inorganic filler particles having a particle size in the range from 7 to 70 nm in the total amount (B1) was determined in the total amount (A) of free-radically polymerizable monomers (cf. the test method for determination of the refractive indices).

In a third step, the respective photoinitiators in the total amount (C), the respective colorants in the total amount (D) and the respective auxiliaries in the total amount (E) were introduced with stirring into the homogenized mixture freed of the solvent which resulted from step 2.

In a fourth step, the respective total amount (B2) of inorganic filler particles having a particle size in the range from 0.12 μm to 10 μm was incorporated by means of a Hauschild AM 501 mixing device into the mixture resulting from the third step and then processed to give a homogeneous pasty mass (4*12 s), which was freed of air at 50 rpm and −0.85 bar in a laboratory kneader with beam stirrers (PC Laborsystem, Magden, CH) for 10 min.

IV. Compositions of the Examples:

IV.1 Inventive Examples

The tables that follow describe, by way of example, the compositions of dental light-curable compositions of the invention for elective production of a visible restoration in the anterior region or for filling of a cavity in the posterior region. All abbreviations correspond to the corresponding materials from table 1.

The mixing ratios used, the materials used, i.e. the free-radically polymerizable monomers in the total amount (A), the nonaggregated and nonagglomerated inorganic filler particles having a particle size in the range from 7 to 70 nm in the total amount (B1), the inorganic filler particles having a particle size in the range from 0.12 μm to 10 μm in the total amount (B2), the photoinitiators in the total amount (C), the colorants in the total amount (D) and the auxiliaries in the total amount (E) are merely illustrative and other concentrations, materials and combinations of materials may also be used; for the corresponding properties see the above description.

The examples are divided into "uncolored" example formulations and "colored" example formulations; cf. the respective names in the first row of the tables that follow. Uncolored example formulations do not contain any colorants in the total amount (D). Colored example formulations contain colorants in the total amount (D).

The tables that follow additionally report the refractive indices of the respective total amounts (A), (B1) and (B2) for the wavelengths of 470 nm (specific blue light) and 589 nm (specific yellow light, sodium D line). The refractive indices were determined by the above-described test methods. Additionally reported in brackets are the differences in refractive index between the total amounts (A) and (B1) (Δn (A), (B1)) and between the total amounts (A) and (B2) (Δn (A), (B2)); here too, each determined at the wavelengths of 470 nm and 589 nm. The differences in refractive index between the total amounts (B1) and (B2) are reported in separate rows; here too, each determined at the wave-lengths of 470 nm ($\Delta\ n_{470\ nm}$ (B1), $n_{470\ nm}$ (B2)) and 589 nm ($\Delta\ n_{589\ nm}$ (B1), $n_{589\ nm}$ (B2)).

Example 1 (Inventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 2.55% | 5.88% | 2.54% | 5.86% |
| | TCD-DMA | 0.44% | 1.09% | 0.44% | 1.09% |
| | Bis-EMA | 10.63% | 25.82% | 10.62% | 25.79% |
| | $n_{A,\ 470\ nm}$ | 1.55430 | | | |
| | $n_{A,\ 589\ nm}$ | 1.54017 | | | |
| (B1) | 20 nm $YbF_3$ + MDP | 29.79% | 11.98% | 29.82% | 12.01% |
| | $n_{B1,\ 470\ nm}$ (Δn (A), (B1)) | 1.54870 (0.00560) | | | |
| | $n_{B1,\ 589\ nm}$ (Δn (A), (B1)) | 1.54216 (−0.00199) | | | |
| (B2) | Glass ceramic 0.7 μm | 9.57% | 9.30% | 9.57% | 9.30% |
| | Glass ceramic 2.0 μm | 46.80% | 45.45% | 46.76% | 45.44% |
| | $n_{B2,\ 470\ nm}$ (Δn (A), (B2)) | 1.53570 (0.01860) | | | |
| | $n_{B2,\ 589\ nm}$ (Δn (A), (B2)) | 1.52800 (0.01217) | | | |
| | $\Delta\ n_{470\ nm}$ (B1), $n_{470\ nm}$ (B2) | 0.01300 | | | |
| | $\Delta\ n_{589\ nm}$ (B1), $n_{589\ nm}$ (B2) | 0.01416 | | | |
| (C) | Camphorquinone | 0.04% | 0.09% | 0.04% | 0.09% |
| | DABE | 0.06% | 0.14% | 0.06% | 0.14% |
| (D) | FS black | — | — | 0.003% | 0.002% |
| | FS white | — | — | 0.01% | 0.006% |
| | FS yellow | — | — | 0.03% | 0.017% |
| | FS red | — | — | 0.004% | 0.002% |
| (E) | BHT | 0.04% | 0.10% | 0.04% | 0.10% |
| | BZT | 0.07% | 0.13% | 0.07% | 0.13% |

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 2.68% | 7.39% | 2.68% | 7.38% |
| | TCD-DMA | 0.28% | 0.83% | 0.28% | 0.82% |
| | Bis-EMA | 5.63% | 16.37% | 5.63% | 16.37% |
| | $n_{A,\ 470\ nm}$ | 1.55600 | | | |
| | $n_{A,\ 589\ nm}$ | 1.54187 | | | |
| (B1) | 50 nm $YbF_3$ + MDP | 45.93% | 22.32% | 45.92% | 22.32% |
| | $n_{B1,\ 470\ nm}$ (Δn (A), (B1)) | 1.54863 (0.00737) | | | |
| | $n_{B1,\ 589\ nm}$ (Δn (A), (B1)) | 1.54209 (−0.00022) | | | |
| (B2) | Glass ceramic 0.7 μm | 7.56% | 8.79% | 7.56% | 8.79% |
| | Glass ceramic 2.0 μm | 37.78% | 43.93% | 37.78% | 43.93% |
| | $n_{B2,\ 470\ nm}$ (Δn (A), (B2)) | 1.53570 (0.02030) | | | |
| | $n_{B2,\ 589\ nm}$ (Δn (A), (B2)) | 1.52800 (0.01387) | | | |
| | $\Delta\ n_{470\ nm}$ (B1), $n_{470\ nm}$ (B2) | 0.01293 | | | |
| | $\Delta\ n_{589\ nm}$ (B1), $n_{589\ nm}$ (B2) | 0.01409 | | | |
| (C) | Camphorquinone | 0.02% | 0.07% | 0.03% | 0.07% |
| | DABE | 0.04% | 0.11% | 0.04% | 0.11% |
| (D) | FS black | — | — | 0.002% | 0.002% |
| | FS yellow | — | — | 0.02% | 0.014% |
| | FS red | — | — | 0.003% | 0.002% |
| (E) | BHT | 0.03% | 0.08% | 0.03% | 0.08% |
| | BZT | 0.04% | 0.10% | 0.04% | 0.10% |

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 3.07% | 8.56% | 3.06% | 8.55% |
| | Bis-EMA | 6.13% | 18.09% | 6.13% | 18.08% |
| | $n_{A,\ 470\ nm}$ | | 1.55600 | | |
| | $n_{A,\ 589\ nm}$ | | 1.54187 | | |
| (B1) | 50 nm $YbF_3$ + MDP | 49.35% | 24.27% | 49.34% | 24.27% |
| | $n_{B1,\ 470\ nm}$ (Δn (A), (B1)) | | 1.54863 (0.00737) | | |
| | $n_{B1,\ 589\ nm}$ (Δn (A), (B1)) | | 1.54209 (−0.00022) | | |
| (B2) | Glass ceramic 0.7 μm | 41.28% | 48.66% | 41.26% | 48.66% |
| | $n_{B2,\ 470\ nm}$ (Δn (A), (B2)) | | 1.53570 (0.02030) | | |
| | $n_{B2,\ 589\ nm}$ (Δn (A), (B2)) | | 1.52800 (0.01387) | | |
| | Δ $n_{470\ nm}$ (B1), $n_{470\ nm}$ (B2) | | 0.01293 | | |
| | Δ $n_{589\ nm}$ (B1), $n_{589\ nm}$ (B2) | | 0.01409 | | |
| (C) | Camphorquinone | 0.03% | 0.08% | 0.03% | 0.08% |
| | DABE | 0.04% | 0.12% | 0.04% | 0.12% |
| (D) | FS black | — | — | 0.003% | 0.002% |
| | FS yellow | — | — | 0.02% | 0.017% |
| | FS red | — | — | 0.004% | 0.002% |
| (E) | BHT | 0.04% | 0.09% | 0.04% | 0.09% |
| | BZT | 0.06% | 0.12% | 0.07% | 0.12% |

Example 4 (Inventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 2.92% | 8.00% | 2.91% | 7.97% |
| | TCD-DMA | 5.14% | 15.10% | 5.12% | 15.05% |
| | Bis-EMA | 0.26% | 0.74% | 0.28% | 0.81% |
| | $n_{A,\ 470\ nm}$ | | 1.52987 | | |
| | $n_{A,\ 589\ nm}$ | | 1.51860 | | |
| (B1) | 50 nm $YbF_3$ + MDP | 44.50% | 21.47% | 44.48% | 21.47% |
| | $n_{B1,\ 470\ nm}$ (Δn (A), (B1)) | | 1.54863 (−0.01876) | | |
| | $n_{B1,\ 589\ nm}$ (Δn (A), (B1)) | | 1.54209 (−0.02349) | | |
| (B2) | Glass ceramic 0.7 μm | 7.84% | 9.06% | 7.84% | 9.05% |
| | Glass ceramic 2.0 μm | 39.21% | 45.28% | 39.19% | 45.26% |
| | $n_{B2,\ 470\ nm}$ (Δn (A), (B2)) | | 1.53570 (−0.00583) | | |
| | $n_{B2,\ 589\ nm}$ (Δn (A), (B2)) | | 1.52800 (−0.00940) | | |
| | Δ $n_{470\ nm}$ (B1), $n_{470\ nm}$ (B2) | | 0.01293 | | |
| | Δ $n_{589\ nm}$ (B1), $n_{589\ nm}$ (B2) | | 0.01409 | | |
| (C) | Camphorquinone | 0.02% | 0.07% | 0.02% | 0.07% |
| | DABE | 0.04% | 0.10% | 0.03% | 0.10% |
| (D) | FS black | — | — | 0.004% | 0.003% |
| | FS white | — | — | 0.014% | 0.010% |
| | FS yellow | — | — | 0.02% | 0.015% |
| | FS red | — | — | 0.004% | 0.002% |
| (E) | BHT | 0.03% | 0.08% | 0.03% | 0.08% |
| | BZT | 0.04% | 0.10% | 0.04% | 0.10% |

Example 5 (Inventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 2.83% | 7.79% | 2.82% | 7.76% |
| | TCD-DMA | 2.78% | 8.20% | 2.77% | 8.17% |
| | Bis-EMA | 2.93% | 8.50% | 2.94% | 8.54% |
| | $n_{A,\ 470\ nm}$ | | 1.54315 | | |
| | $n_{A,\ 589\ nm}$ | | 1.53044 | | |
| (B1) | 50 nm $YbF_3$ + MDP | 45.64% | 22.13% | 45.62% | 22.13% |
| | $n_{B1,\ 470\ nm}$ (Δn (A), (B1)) | | 1.54863 (−0.00548) | | |
| | $n_{B1,\ 589\ nm}$ (Δn (A), (B1)) | | 1.54209 (−0.01165) | | |
| (B2) | Glass ceramic 0.7 μm | 7.62% | 8.84% | 7.61% | 8.84% |
| | Glass ceramic 2.0 μm | 38.08% | 44.18% | 38.06% | 44.17% |
| | $n_{B2,\ 470\ nm}$ (Δn (A), (B2)) | | 1.53570 (0.00745) | | |
| | $n_{B2,\ 589\ nm}$ (Δn (A), (B2)) | | 1.52800 (0.00244) | | |

-continued

| Total amount | Materials/ refractive indices | Uncolored | | Colored | |
|---|---|---|---|---|---|
| | | [% by wt.] | [% by vol.] | [% by wt.] | [% by vol.] |
| | $\Delta$ $n_{470\ nm}$ (B1), $n_{470\ nm}$ (B2) | 0.01293 | | | |
| | $\Delta$ $n_{589\ nm}$ (B1), $n_{589\ nm}$ (B2) | 0.01409 | | | |
| (C) | Camphorquinone | 0.02% | 0.07% | 0.02% | 0.07% |
| | DABE | 0.04% | 0.11% | 0.04% | 0.10% |
| (D) | FS black | — | — | 0.004% | 0.003% |
| | FS white | — | — | 0.009% | 0.007% |
| | FS yellow | — | — | 0.02% | 0.017% |
| | FS red | — | — | 0.004% | 0.0024% |
| (E) | BHT | 0.03% | 0.08% | 0.03% | 0.08% |
| | BZT | 0.04% | 0.10% | 0.04% | 0.10% |

Example 6 (Inventive, Uncolored and Colored)

| Total amount | Materials/ refractive indices | Uncolored | | Colored | |
|---|---|---|---|---|---|
| | | [% by wt.] | [% by vol.] | [% by wt.] | [% by vol.] |
| (A) | Bis-GMA | 5.36% | 14.83% | 5.35% | 14.80% |
| | TCD-DMA | 0.28% | 0.83% | 0.28% | 0.82% |
| | Bis-EMA | 2.95% | 8.60% | 2.96% | 8.63% |
| | $n_{A,\ 470\ nm}$ | 1.56034 | | | |
| | $n_{A,\ 589\ nm}$ | 1.54610 | | | |
| (B1) | 50 nm $YbF_3$ + MDP | 45.92% | 22.41% | 45.91% | 22.41% |
| | $n_{B1,\ 470\ nm}$ ($\Delta$n (A), (B1)) | 1.54863 (0.01171) | | | |
| | $n_{B1,\ 589\ nm}$ ($\Delta$n (A), (B1)) | 1.54209 (0.00401) | | | |
| (B2) | Glass ceramic 0.7 µm | 7.58% | 8.85% | 7.58% | 8.85% |
| | Glass ceramic 2.0 µm | 37.78% | 44.11% | 37.77% | 44.10% |
| | $n_{B2,\ 470\ nm}$ ($\Delta$n (A), (B2)) | 1.53570 (0.02464) | | | |
| | $n_{B2,\ 589\ nm}$ ($\Delta$n (A), (B2)) | 1.52800 (0.01810) | | | |
| | $\Delta$ $n_{470\ nm}$ (B1), $n_{470\ nm}$ (B2) | 0.01293 | | | |
| | $\Delta$ $n_{589\ nm}$ (B1), $n_{589\ nm}$ (B2) | 0.01409 | | | |
| (C) | Camphorquinone | 0.02% | 0.07% | 0.02% | 0.07% |
| | DABE | 0.04% | 0.11% | 0.04% | 0.11% |
| (D) | FS black | — | — | 0.003% | 0.002% |
| | FS yellow | — | — | 0.02% | 0.014% |
| | FS red | — | — | 0.003% | 0.0020% |
| (E) | BHT | 0.03% | 0.08% | 0.03% | 0.08% |
| | BZT | 0.04% | 0.10% | 0.04% | 0.10% |

Example 7 (Inventive, Uncolored and Colored)

| Total amount | Materials/ refractive indices | Uncolored | | Colored | |
|---|---|---|---|---|---|
| | | [% by wt.] | [% by vol.] | [% by wt.] | [% by vol.] |
| (A) | Bis-GMA | 2.53% | 5.79% | 2.52% | 5.77% |
| | TCD-DMA | 0.44% | 1.07% | 0.44% | 1.07% |
| | Bis-EMA | 10.53% | 25.41% | 10.51% | 25.39% |
| | $n_{A,\ 470\ nm}$ | 1.55430 | | | |
| | $n_{A,\ 589\ nm}$ | 1.54017 | | | |
| (B1) | 15 nm $YbF_3$ + MDP | 29.77% | 12.66% | 29.81% | 12.68% |
| | $n_{B1,\ 470\ nm}$ ($\Delta$n (A), (B1)) | 1.54347 (0.01083) | | | |
| | $n_{B1,\ 589\ nm}$ ($\Delta$n (A), (B1)) | 1.53684 (0.00333) | | | |
| (B2) | Glass ceramic 0.7 µm | 9.42% | 9.10% | 9.41% | 9.10% |
| | Glass ceramic 2.0 µm | 47.11% | 45.49% | 47.07% | 45.48% |
| | $n_{B2,\ 470\ nm}$ ($\Delta$n (A), (B2)) | 1.53570 (0.01860) | | | |
| | $n_{B2,\ 589\ nm}$ ($\Delta$n (A), (B2)) | 1.52800 (0.01217) | | | |
| | $\Delta$ $n_{470\ nm}$ (B1), $n_{470\ nm}$ (B2) | 0.00777 | | | |
| | $\Delta$ $n_{589\ nm}$ (B1), $n_{589\ nm}$ (B2) | 0.00884 | | | |
| (C) | Camphorquinone | 0.04% | 0.09% | 0.04% | 0.09% |
| | DABE | 0.06% | 0.14% | 0.06% | 0.14% |
| (D) | FS black | — | — | 0.005% | 0.002% |
| | FS white | — | — | 0.008% | 0.005% |
| | FS yellow | — | — | 0.02% | 0.014% |
| | FS red | — | — | 0.004% | 0.0020% |

-continued

| Total amount | Materials/ refractive indices | Uncolored [% by wt.] | Uncolored [% by vol.] | Colored [% by wt.] | Colored [% by vol.] |
|---|---|---|---|---|---|
| (E) | BHT | 0.04% | 0.10% | 0.04% | 0.10% |
| | BZT | 0.07% | 0.13% | 0.07% | 0.13% |

Example 8 (Inventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 0.95% | 2.61% | 0.95% | 2.60% |
| | TCD-DMA | 0.27% | 0.80% | 0.27% | 0.80% |
| | Bis-EMA | 7.22% | 20.90% | 7.22% | 20.89% |
| | $n_{A,\ 470\ nm}$ | | 1.55284 | | |
| | $n_{A,\ 589\ nm}$ | | 1.53876 | | |
| (B1) | 50 nm $YbF_3$ + MDP | 45.20% | 21.86% | 45.19% | 21.86% |
| | $n_{B1,\ 470\ nm}$ (Δn (A), (B1)) | | 1.54863 (0.004219) | | |
| | $n_{B1,\ 589\ nm}$ (Δn (A), (B1)) | | 1.54209 (−0.00333) | | |
| (B2) | Glass ceramic 0.7 μm | 7.70% | 8.91% | 7.70% | 8.91% |
| | Glass ceramic 2.0 μm | 38.51% | 44.56% | 38.51% | 44.56% |
| | $n_{B2,\ 470\ nm}$ (Δn (A), (B2)) | | 1.53570 (0.01714) | | |
| | $n_{B2,\ 589\ nm}$ (Δn (A), (B2)) | | 1.52800 (0.01076) | | |
| | Δ $n_{470\ nm}$ (B1), $n_{470\ nm}$ (B2) | | 0.01293 | | |
| | Δ $n_{589\ nm}$ (B1), $n_{589\ nm}$ (B2) | | 0.01409 | | |
| (C) | Camphorquinone | 0.02% | 0.07% | 0.02% | 0.07% |
| | DABE | 0.04% | 0.11% | 0.04% | 0.11% |
| (D) | FS black | — | — | 0.003% | 0.002% |
| | FS yellow | — | — | 0.02% | 0.013% |
| | FS red | — | — | 0.003% | 0.0020% |
| (E) | BHT | 0.03% | 0.08% | 0.03% | 0.08% |
| | BZT | 0.04% | 0.10% | 0.04% | 0.10% |

Example 9 (Inventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | UDMA | 8.61% | 14.06% | 8.60% | 14.05% |
| | TEDMA | 9.83% | 16.50% | 9.82% | 16.49% |
| | $n_{A,\ 470\ nm}$ | | 1.48123 | | |
| | $n_{A,\ 589\ nm}$ | | 1.47224 | | |
| (B1) | 50 nm SiO2 + MPS | 28.44 | 25.56% | 28.44% | 25.56% |
| | $n_{B1,\ 470\ nm}$ (Δn (A), (B1)) | | 1.46660 (0.01463) | | |
| | $n_{B1,\ 589\ nm}$ (Δn (A), (B1)) | | 1.46070 (0.01154) | | |
| | Quartz glass 0.7 μm | 52.79% | 43.40% | 52.78% | 43.40% |
| | $n_{B2,\ 470\ nm}$ (Δn (A), (B2)) | | 1.46410 (0.01713) | | |
| | $n_{B2,\ 589\ nm}$ (Δn (A), (B2)) | | 1.45840 (0.01384) | | |
| | Δ $n_{470\ nm}$ (B1), $n_{470\ nm}$ (B2) | | 0.00250 | | |
| | Δ $n_{589\ nm}$ (B1), $n_{589\ nm}$ (B2) | | 0.00230 | | |
| (C) | Camphorquinone | 0.05% | 0.09% | 0.05% | 0.09% |
| | DABE | 0.08% | 0.13% | 0.08% | 0.13% |
| (D) | FS black | — | — | 0.003% | 0.001% |
| | FS white | — | — | 0.007% | 0.01% |
| | FS yellow | — | — | 0.02% | 0.014% |
| | FS red | — | — | 0.004% | 0.002% |
| (E) | BHT | 0.07% | 0.11% | 0.07% | 0.11% |
| | BZT | 0.12% | 0.14% | 0.12% | 0.14% |

IV.2 Noninventive Examples

The tables that follow relate by way of example to the compositions of noninventive dental light-curable compositions.

Example 10 (Noninventive, Uncolored and Colored)

| Total amount | Materials/ refractive indices | Uncolored [% by wt.] | Uncolored [% by vol.] | Colored [% by wt.] | Colored [% by vol.] |
|---|---|---|---|---|---|
| (A) | Bis-GMA | 4.17% | 7.77% | 4.16% | 7.74% |
| | TCD-DMA | 0.43% | 0.86% | 0.43% | 0.86% |
| | Bis-EMA | 8.76% | 17.19% | 8.72% | 17.13% |
| | $n_{A,\ 470\ nm}$ | 1.55600 | | | |
| | $n_{A,\ 589\ nm}$ | 1.54187 | | | |
| (B1) | 50 nm $SiO_2$ + MPS | 20.52% | 22.05% | 20.61% | 22.15% |
| | $n_{B1,\ 470\ nm}$ (Δn (A), (B1)) | 1.46660 (0.08940) | | | |
| | $n_{B1,\ 589\ nm}$ (Δn (A), (B1)) | 1.46070 (0.08117) | | | |
| (B2) | Glass ceramic 0.7 μm | 12.01% | 9.43% | 11.99% | 9.42% |
| | Glass ceramic 2.0 μm | 53.91% | 42.32% | 53.83% | 42.29% |
| | $n_{B2,\ 470\ nm}$ (Δn (A), (B2)) | 1.53570 (0.02030) | | | |
| | $n_{B2,\ 589\ nm}$ (Δn (A), (B2)) | 1.52800 (0.01387) | | | |
| | Δ $n_{470\ nm}$ (B1), $n_{470\ nm}$ (B2) | −0.06910 | | | |
| | Δ $n_{589\ nm}$ (B1), $n_{589\ nm}$ (B2) | −0.06730 | | | |
| (C) | Camphorquinone | 0.04% | 0.07% | 0.04% | 0.08% |
| | DABE | 0.06% | 0.11% | 0.06% | 0.11% |
| (D) | FS black | — | — | 0.003% | 0.001% |
| | FS white | — | — | 0.01% | 0.01% |
| | FS yellow | — | — | 0.03% | 0.018% |
| | FS red | — | — | 0.005% | 0.002% |
| (E) | BHT | 0.04% | 0.08% | 0.04% | 0.08% |
| | BZT | 0.07% | 0.11% | 0.07% | 0.10% |

The dental compositions according to example 10 (uncolored or colored) have good mechanical properties; however, the refractive indices of the materials used are not matched to one another in an inventive manner. Details in this regard can be found in section IV.3 below. Consequences with regard to the properties of depth of cure and translucence are apparent from section V.1.

Example 11 and 12 (Noninventive, Uncolored)

| Total amount | Materials/ refractive indices | Example 11 [% by wt.] | Example 11 [% by vol.] | Example 12 [% by wt.] | Example 12 [% by vol.] |
|---|---|---|---|---|---|
| (A) | Bis-GMA | 6.53% | 12.60% | 5.28% | 11.34% |
| | TCD-DMA | 0.68% | 1.40% | 0.55% | 1.26% |
| | Bis-EMA | 13.70% | 27.89% | 11.09% | 25.10% |
| | $n_{A,\ 470\ nm}$ | 1.55600 | | 1.55600 | |
| | $n_{A,\ 589\ nm}$ | 1.54187 | | 1.54187 | |
| (B1) | 50 nm $YbF_3$ + MDP | 13.94% | 4.70% | 24.92% | 9.34% |
| | $n_{B1,\ 470\ nm}$ (Δn (A), (B1)) | 1.54863 (0.00737) | | 1.54863 (0.00737) | |
| | $n_{B1,\ 589\ nm}$ (Δn (A), (B1)) | 1.54209 (−0.00022) | | 1.54209 (−0.00022) | |
| (B2) | Glass ceramic 0.7 μm | 10.81% | 8.80% | 9.65% | 8.74% |
| | Glass ceramic 2.0 μm | 54.05% | 44.02% | 48.26% | 43.69% |
| | $n_{B2,\ 470\ nm}$ (Δn (A), (B2)) | 1.53570 (0.02030) | | 1.53570 (0.02030) | |
| | $n_{B2,\ 589\ nm}$ (Δn (A), (B2)) | 1.52800 (0.01387) | | 1.52800 (0.01387) | |
| | Δ $n_{470\ nm}$ (B1), $n_{470\ nm}$ (B2) | 0.01293 | | 0.01293 | |
| | Δ $n_{589\ nm}$ (B1), $n_{589\ nm}$ (B2) | 0.01409 | | 0.01409 | |
| (C) | Camphorquinone | 0.06% | 0.12% | 0.05% | 0.11% |
| | DABE | 0.09% | 0.18% | 0.07% | 0.17% |
| (E) | BHT | 0.06% | 0.13% | 0.05% | 0.11% |
| | BZT | 0.10% | 0.16% | 0.08% | 0.14% |

Example 13-14 (Noninventive, Uncolored)

| Total amount | Materials/ refractive indices | Example 13 [% by wt.] | Example 13 [% by vol.] | Example 14 [% by wt.] | Example 14 [% by vol.] |
|---|---|---|---|---|---|
| (A) | Bis-GMA | 3.55% | 10.32% | 3.91% | 11.64% |
| | TCD-DMA | 0.37% | 1.15% | 0.41% | 1.30% |
| | Bis-EMA | 7.45% | 22.84% | 8.20% | 25.76% |
| | $n_{A,\ 470\ nm}$ | 1.55600 | | 1.55600 | |
| | $n_{A,\ 589\ nm}$ | 1.54187 | | 1.54187 | |
| (B1) | 50 nm $YbF_3$ + MDP | 60.72% | 31.14% | 66.91% | 35.13% |
| | $n_{B1,\ 470\ nm}$ (Δn (A), (B1)) | 1.54863 (0.00737) | | 1.54863 (0.00737) | |
| | $n_{B1,\ 589\ nm}$ (Δn (A), (B1)) | 1.54209 (−0.00022) | | 1.54209 (−0.00022) | |
| (B2) | Glass ceramic 0.7 μm | 4.62% | 5.67% | 3.40% | 4.27% |
| | Glass ceramic 2.0 μm | 23.12% | 28.37% | 16.98% | 21.33% |
| | $n_{B2,\ 470\ nm}$ (Δn (A), (B2)) | 1.53570 (0.02030) | | 1.53570 (0.02030) | |
| | $n_{B2,\ 589\ nm}$ (Δn (A), (B2)) | 1.52800 (0.01387) | | 1.52800 (0.01387) | |
| | $\Delta\ n_{470\ nm}$ (B1), $n_{470\ nm}$ (B2) | 0.01293 | | 0.01293 | |
| | $\Delta\ n_{589\ nm}$ (B1), $n_{589\ nm}$ (B2) | 0.01409 | | 0.01409 | |
| (C) | Camphorquinone | 0.03% | 0.10% | 0.04% | 0.11% |
| | DABE | 0.05% | 0.15% | 0.05% | 0.17% |
| (E) | BHT | 0.03% | 0.11% | 0.04% | 0.12% |
| | BZT | 0.06% | 0.14% | 0.06% | 0.16% |

| Total amount | Materials/ refractive indices | Uncolored [% by wt.] | Uncolored [% by vol.] |
|---|---|---|---|
| (A) | Bis-GMA | 7.86% | 13.58% |
| | TCD-DMA | 0.81% | 1.51% |
| | Bis-EMA | 16.51% | 30.05% |
| | $n_{A,\ 470\ nm}$ | 1.55600 | |
| | $n_{A,\ 589\ nm}$ | 1.54187 | |
| (B2) | Glass ceramic 0.7 μm | 12.41% | 9.03% |
| | Glass ceramic 2.0 μm | 62.02% | 45.16% |
| | $n_{B2,\ 470\ nm}$ (Δn (A), (B2)) | 1.53570 (0.02030) | |
| | $n_{B2,\ 589\ nm}$ (Δn (A), (B2)) | 1.52800 (0.01387) | |
| (C) | Camphorquinone | 0.07% | 0.13% |
| | DABE | 0.11% | 0.20% |
| (E) | BHT | 0.08% | 0.14% |
| | BZT | 0.13% | 0.18% |

Example 15 (Noninventive, Uncolored)

IV.3 Distinction of the Examples

The dental light-curable compositions (examples 1-15) are distinguished as follows:

The inventive dental light-curable compositions 1-9 comprise a total amount (A) of free-radically polymerizable monomers, a total amount (B1) of nonaggregated and nonagglomerated inorganic filler particles having a particle size in the range from 7 to 70 nm, and a total amount (B2) of inorganic filler particles having a particle size in the range from 0.12 μm to 10 μm.

In the inventive dental light-curable compositions 1-9, the materials and the mixing ratios of the free-radically polymerizable monomers in the respective total amounts (A) are selected and matched to one another such that the total amount (A) in each case has a refractive index $n_{A,\ 470\ nm}$ in the range from 1.470 to 1.560 (cf. the corresponding table entries $n_{A,\ 470\ nm}$ of the inventive dental light-curable dental materials 1-9).

nonaggregated and nonagglomerated inorganic filler particles having a particle size in the range from 7 to 70 nm in the respective total amounts (B1) are selected and matched to one another such that the total amount (B1) in each case has a refractive index $n_{B1,\ 470\ nm}$ in the range from 1.460 to 1.570 (cf. the corresponding table entries $n_{B1,\ 470\ nm}$ of the inventive dental light-curable dental materials 1-9).

inorganic filler particles having a particle size in the range from 0.12 μm to 10 μm in the respective total amounts (B2) are selected and matched to one another such that the total amount (B2) in each case has a refractive index $n_{B2,\ 470\ nm}$ in the range from 1.450 to 1.560 (cf. the corresponding table entries $n_{B2,\ 470\ nm}$ of the inventive dental light-curable dental materials 1-9).

In the inventive dental light-curable compositions 1-9, it is additionally the case that the refractive indices of the respective total amount (A) of free-radically polymerizable monomers and of the respective total amount (B1) of nonaggregated and nonagglomerated inorganic filler particles having a particle size in the range from 7 to 70 nm are matched to one another such that the following condition is met:

$$n_{B1,470\ nm}-0.025<n_{A,470\ nm}<n_{B1,470\ nm}+0.030$$

(cf. the corresponding table entries Δn (A), (B1) for the inventive dental light-curable compositions 1-9).

It is also the case in the inventive dental light-curable compositions 1-9 that the refractive indices of the respective total amount (A) of free-radically polymerizable monomers and of the respective total amount (B2) of inorganic filler particles having a particle size in the range from 0.12 μm to 10 μm are matched to one another such that the following condition is met:

$$n_{B2,470\ nm}-0.015<n_{A,470\ nm}<n_{B2,470\ nm}+0.040$$

(cf. the corresponding table entries Δn (A), (B2) for the inventive dental light-curable compositions 1-9).

It is also the case in the inventive dental light-curable compositions 1-9 that the refractive indices of the respective total amount (B1) of nonaggregated and nonagglomerated inorganic filler particles having a particle size in the range from 7 to 70 nm and of the respective total amount (B2) of inorganic filler particles having a particle size in the range from 0.12 μm to 10 μm are matched to one another such that the following condition is met:

$$n_{B2,470\ nm}-0.020<n_{B1,470\ nm}<n_{B2,470\ nm}+0.035$$

(cf. the corresponding table entries $\Delta n_{470\,nm}$ (B1), $n_{470\,nm}$ (B2) for the inventive dental light-curable compositions 1-9).

The inventive dental light-curable compositions 1-9 comprise a total amount (B1) of nonaggregated and nonagglomerated inorganic filler particles having a particle size in the range from 7 to 70 nm, where this total amount (B1) is in the range from 10 to 30 percent by volume, based on the respective overall dental light-curable composition (cf. the corresponding table entries in the "[% by vol.]" column for row "(B1)" for the inventive dental light-curable compositions 1-9).

The inventive dental light-curable compositions 1-9 comprise a total amount (B1) of nonaggregated and nonagglomerated inorganic filler particles having a particle size in the range from 7 to 70 nm. These filler particles differ with regard to their particle sizes as follows (the reported particle sizes are the d50 values in volume-weighted evaluation; cf. in this regard also the details relating to the test method):

Example 1: $YbF_3$+MDP; 20 nm
Examples 2-6 and 8: $YbF_3$+MDP; 50 nm
Example 7: $YbF_3$+MDP; 15 nm
Example 9: $SiO_2$+MPS; 50 nm The inventive dental light-curable compositions 1-9 additionally comprise a total amount (C) of photoinitiators (camphorquinone and DABE), a total amount (D) of colorants (colored examples 1-9) or no total amount (D) of colorants (uncolored examples 1-9), and a total amount (E) of auxiliaries (BHT as inhibitor and BZT as UV stabilizer).

Noninventive example 10 (colored and uncolored) comprises a total amount (A) of free-radically polymerizable monomers and a total amount (B1) of nonaggregated and nonagglomerated inorganic filler particles having a particle size in the range from 7 to 70 nm ($SiO_2$+MPS; 50 nm), where the refractive index of the total amount (A) measured at a wavelength of 470 nm is 1.55600, the refractive index of the total amount (B1), likewise measured at a wavelength of 470 nm, is 1.46660 ($\Delta n_{470\,nm}$ (A), (B1)=0.08940), and the refractive index of the total amount (B2), likewise measured at a wave-length of 470 nm, is 1.53570 ($\Delta n_{470\,nm}$ (B1), $n_{470\,nm}$ (B2)=−0.06910). Thus, in example 10, the following conditions are not met:

$$n_{B1,470\,nm}-0.025<n_{A,470\,nm}<n_{B1,470\,nm}+0.030 \text{ and}$$

$$n_{B2,470\,nm}-0.020<n_{B1,470\,nm}<n_{B2,470\,nm}+0.035.$$

Noninventive examples 11 and 12 comprise a total amount (B1) of nonaggregated and nonagglomerated inorganic filler particles having a particle size in the range from 7 to 70 nm, where this total amount (B1) is below 10 percent by volume, based on the overall dental light-curable composition (cf. the corresponding table entries in the "[% by vol.]" column for row "(B1)" for the noninventive dental light-curable compositions 11 and 12).

Noninventive examples 13 and 14 comprise a total amount (B1) of nonaggregated and nonagglomerated inorganic filler particles having a particle size in the range from 7 to 70 nm, where this total amount (B1) is above 30 percent by volume, based on the overall dental light-curable composition (cf. the corresponding table entries in the "[% by vol.]" column for row "(B1)" for the noninventive dental light-curable compositions 13 and 14).

Noninventive example 15 does not comprise any total amount (B1) of nonaggregated and nonagglomerated inorganic filler particles having a particle size in the range from 7 to 70 nm.

V. Properties of the Examples

V.1 Depth of Cure and Translucence:

The depth of cure and translucence of inventive dental light-curable compositions are especially determined by the refractive indices of the free-radically polymerizable monomers present therein ($n_{A,\,470\,nm}$ of the total amount (A)) and the refractive indices of the filler particles ($n_{B1,\,470\,nm}$ of the total amount (B1) and $n_{B2,\,470\,nm}$ of the total amount (B2)). Inventive examples 1-9 are compared hereinafter with noninventive example 10 comprising materials (total amounts (A), (B1) and (B2)) that have not been matched to one another in the inventive manner with regard to their refractive indices.

Table 2 below shows:

- depth of cure (depth of polymerization) on incidence of light from an LED (from the Celalux 2 device) with a radiation flux maximum at a wavelength in the range from 440 to 490 nm, an irradiation time of 10 s and an irradiation intensity of 1000 mW/cm$^2$ (DHT 10 s (1000 mW/cm$^2$) [mm]),
- depth of cure on incidence of light from an LED with a radiation flux maximum at a wavelength in the range from 440 to 490 nm, an irradiation time of 20 s and an irradiation intensity of 1000 mW/cm$^2$ (DHT 20 s (1000 mW/cm$^2$) [mm]),
- translucence in % (determined after light curing) and
- color values L*a*b*
- of the inventive dental light-curable compositions (examples 1-9) and of a noninventive dental light-curable composition (example 10). The measurement values listed in table 2 were determined here by means of the test methods described above. When no measurements were conducted, a hyphen "-" is entered in the fields of the tables in each case.

TABLE 2

| Example | | DHT 10 s (1000 mW/cm$^2$) [mm] | DHT 20 s (1000 mW/cm$^2$) [mm] | Translucence [%] | L* | a* | b* |
|---|---|---|---|---|---|---|---|
| 1 | uncolored | ≥6.00 | — | 32.8 | — | — | — |
| | colored | 3.75 | 4.07 | 20.1 | 68.31 | 3.34 | 15.02 |
| 2 | uncolored | 5.21 | — | 28.5 | — | — | — |
| | colored | 3.96 | 4.36 | 20.5 | 65.88 | 3.38 | 15.31 |
| 3 | uncolored | ≥6.00 | — | 28.1 | — | — | — |
| | colored | 3.80 | 4.17 | 18.2 | 68.29 | 3.11 | 15.47 |
| 4 | uncolored | ≥6.00 | — | 41.4 | — | — | — |
| | colored | 3.57 | 4.19 | 20.2 | 65.86 | 3.58 | 14.95 |
| 5 | uncolored | 5.93 | — | 32.2 | — | — | — |
| | colored | 3.78 | 4.24 | 18.5 | 64.4 | 3.23 | 14.12 |
| 6 | uncolored | 5.45 | — | 27.4 | — | — | — |
| | colored | 4.57 | 5.05 | 19.8 | 65.95 | 3.26 | 14.53 |
| 7 | uncolored | ≥6.00 | — | 32.5 | — | — | — |
| | colored | 3.91 | 4.30 | 20.3 | 65.15 | 3.21 | 13.32 |

TABLE 2-continued

| Example | | DHT 10 s (1000 mW/cm$^2$) [mm] | DHT 20 s (1000 mW/cm$^2$) [mm] | Translucence [%] | L* | a* | b* |
|---|---|---|---|---|---|---|---|
| 8 | uncolored | 5.34 | — | 27.8 | — | — | — |
| | colored | 4.30 | 4.72 | 21.4 | 65.04 | 3.33 | 15.42 |
| 9 | uncolored | 5.15 | — | 29.9 | — | — | — |
| | colored | 3.61 | 3.97 | 18.4 | 68.15 | 3.01 | 15.94 |
| 10 (ni) | uncolored | 4.23 | — | 33.6 | — | — | — |
| | colored | 2.88 | — | 18.7 | 66.52 | 3.94 | 16.61 |

ni = noninventive (owing to mutually unmatched refractive indices of the constituents)

It is apparent from the above table 2 that the inventive dental light-curable compositions of examples 1-9 (colored and uncolored) meet the following conditions:

1.) a depth of cure of 3.5 mm or more on incidence of light from an LED (from the Celalux 2 device) with a radiation flux maximum at a wavelength in the range from 440 to 490 nm, an irradiation time of 10 s and an irradiation intensity of 1000 mW/cm$^2$, and 2.) a translucence of less than 45% (after light curing).

The noninventive dental light-curable composition from example 10 (colored), by contrast, has a depth of cure determined on incidence of light from an LED (from the Celalux 2 device) with a radiation flux maximum at a wavelength in the range from 440 to 490 nm, an irradiation time of 10 s and an irradiation intensity of 1000 mW/cm$^2$ (DHT 10 s) of only 2.88 mm.

Example 10 (uncolored) does give a DHT 10 s of 4.23 mm. However, since exclusively colored compositions are used in dental practice, especially in the case of use of a dental light-curable composition in the anterior region, this value already shows that the uncolored dental light-curable composition of example 10 is barely usable as base composition for practical use, since the result would be a product having too low a DHT 10 s with feasible coloring.

The ascertained value of 4.23 mm for example 10 (uncolored) is much lower than the ascertained value of 5.15 mm for example 9 (uncolored). Example 9 is the inventive example with the lowest DHT 10 s among the group of examples 1-9 (each uncolored). Table 2 thus shows impressively that example 10 (uncolored), on account of the mutually unmatched refractive indices of the total amounts of (A) relative to (B1), i.e. the inequation $n_{B1,\ 470\ nm}-0.025<n_{A,\ 470\ nm}<n_{B1,\ 470\ nm}+0.030$ is not satisfied, and on account of the likewise mutually unmatched refractive indices of the total amounts (B1) relative to (B2), the inequation $n_{B2,\ 470\ nm}-0.020<n_{B1,\ 470\ nm}<n_{B2,\ 470\ nm}+0.035$ is likewise not satisfied, by contrast with inventive examples 1-9 (uncolored), is unsuitable as base composition for colored compositions for filling of a cavity in the posterior region.

The depth of cure of the uncolored inventive dental light-curable compositions of examples 1-9, determined on incidence of light from an LED having a radiation flux maximum at a wavelength in the range from 440 to 490 nm, an irradiation time of 10 s and an irradiation intensity of 1000 mW/cm$^2$, are 5.15 mm or more; the uncolored inventive examples 1, 3, 4 and 7 even have depth of cure of 6.00 mm.

V.2 Mechanical Properties:

A dental light-curable composition for production of a visible restoration in the anterior region and for filling of a cavity in the posterior region should preferably in each case have excellent physical and mechanical properties, as described more particularly by the parameters of modulus of elasticity, ACTA abrasion and polymerization shrinkage.

Comparison of the mechanical properties of inventive example compositions 1-9 (containing nano-particles of the total amount (B1) within a range from 10 to 30 percent by volume, based on the overall dental light-curable composition) with the noninventive example compositions 11-15 (11 and 12: total amount (B1)<10 percent by volume; 13 and 14: total amount (B1)>30 percent by volume; 15: without nanoparticles) confirms that light-curable compositions having a percentage of nanoparticles of less than 10 percent by volume or of more than 30 percent by volume, and compositions without nanoparticles, are barely suitable as modern dental composites owing to suboptimal mechanical properties. These compositions in particular do not meet the modern demands on the mechanical properties of dental light-curable compositions suitable for elective production of a visible restoration in the anterior region or for filling of a cavity in the posterior region.

Table 3 below shows modulus of elasticity [GPa], ACTA abrasion [μm] and polymerization shrinkage [%] of inventive example compositions 1-9 and of noninventive example compositions 11-15. The properties listed in table 3 were determined here by means of the test methods described above.

TABLE 3

| Example | Modulus of elasticity [GPa] | ACTA abrasion [μm] | Polymerization shrinkage [%] |
|---|---|---|---|
| 1 | 11.0 | 65 | 1.7 |
| 2 | 14.5 | 48 | 1.3 |
| 3 | 12.3 | 58 | 1.4 |
| 4 | 13.2 | 49 | 1.4 |
| 5 | 13.5 | 47 | 1.3 |
| 6 | 13.7 | 45 | 1.1 |
| 7 | 10.7 | 66 | 1.7 |
| 8 | 13.6 | 45 | 1.4 |
| 9 | 10.7 | 59 | 1.7 |
| 11 (ni) | 9.8 | 83 | 1.9 |
| 12 (ni) | 10.5 | 76 | 1.8 |
| 13 (ni) | 8.2 | 85 | 3.0 |
| 14 (ni) | 7.3 | 98 | 3.7 |
| 15 (ni) | 9.7 | 83 | 2.0 |

ni = noninventive

The comparison shows that the inventive dental light-curable compositions of examples 1-9 (containing nonaggregated and nonagglomerated inorganic filler particles in the total amount (B1) having a particle size in the range from 7 to 70 nm, where this total amount is in the range from 10 to 30 percent by volume, based on the overall dental light-curable composition) have better mechanical properties than the noninventive dental light-curable compositions of examples 11-15 (total amount (B1)<10 percent by volume; >30 percent by volume; or without any total amount (B1)).

The measured values of modulus of elasticity of inventive example compositions 1-9 are in the range from 10.7 GPa to 14.5 GPa, and are thus advantageously higher than the measured values of modulus of elasticity of noninventive example compositions 11-15 (values in the range from 7.3 GPa to 10.5 GPa).

The measured values of ACTA abrasion of inventive example compositions 1-9 are in the range from 45 μm to 66 μm, and are thus advantageously lower than the measured values of ACTA abrasion of noninventive example compositions 11-15 (values in the range from 76 μm to 98 μm).

The measured values of polymerization shrinkage of inventive example compositions are in the range from 1.1% to 1.7%, and are thus advantageously lower than the measured values of polymerization shrinkage of noninventive example compositions 11-15 (values in the range from 1.8% to 3.7%).

It is thus found that the inventive dental light-curable compositions for elective production of a visible restoration in the anterior region or for filling of a cavity in the posterior region have an advantageous technical effect in relation to:

i) distinctly higher strength of the cured dental light-curable composition (high modulus of elasticity) and
ii) distinctly higher abrasion resistance of the cured dental light-curable composition (low ACTA abrasion) and
iii) distinctly reduced shrinkage on curing (very low polymerization shrinkage).

By comparison, none of the noninventive example compositions meets the overall requirements in relation to mechanical properties.

We claim:

1. A dental light-curable composition for elective production of a visible restoration in the anterior region or for filling of a cavity in the posterior region, comprising a total amount (A) of free-radically polymerizable monomers, where this total amount (A) consists of one, two, three or more than three free-radically polymerizable monomers and has a refractive index $n_{A,\ 470\ nm}$ in the range from 1.470 to 1.560, a total amount (B1) of nonaggregated and nonagglomerated inorganic filler particles having a particle size in the range from 7 to 70 nm, where this total amount (B1) has a refractive index $n_{B1,\ 470\ nm}$ in the range from 1.460 to 1.570 and where this total amount (B1) is in the range from 10 to 30 percent by volume, based on the overall dental light-curable composition, a total amount (B2) of inorganic filler particles having a particle size in the range from 0.12 μm to 10 μm, where this total amount (B2) has a refractive index $n_{B2,\ 470\ nm}$ in the range from 1.450 to 1.560, and a total amount (C) of photoinitiators, where the following condition applies to the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.025<n_{A,470\ nm}<n_{B1,470\ nm}+0.030$$

and where the following condition applies to the refractive indices of the total amount (A) of free-radically polymerizable monomers and the total amount (B2) of inorganic filler particles having a particle size in the range from 0.12 μm to 10 μm:

$$n_{B2,470\ nm}-0.015<n_{A,470\ nm}<n_{B2,470\ nm}+0.040$$

and where the following condition applies to the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.020<n_{B1,470\ nm}<n_{B2,470\ nm}+0.035.$$

2. The dental light-curable composition as claimed in claim 1, wherein the total amount (A) of free-radically polymerizable monomers, the total amount (B1) of nonaggregated and nonagglomerated inorganic filler particles having a particle size in the range from 7 to 70 nm, the total amount (B2) of inorganic filler particles having a particle size in the range from 0.12 μm to 10 μm, and the total amount (C) of photoinitiators is chosen such that the dental light-curable composition has a depth of cure of 3.5 mm or more on incidence of light from an LED with a radiation flux maximum at a wavelength in the range from 440 to 490 nm, an irradiation time of 10 s and an irradiation intensity of 1000 $mW/cm^2$, and/or the dental light-curable composition after curing has a translucence of less than 45%.

3. The dental light-curable composition as claimed in claim 1, wherein the following condition applies to the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.020<n_{A,470\ nm}<n_{B1,470\ nm}+0.025,$$

and/or where the following condition applies to the refractive indices of the total amount (A) of free-radically polymerizable monomers and the total amount (B2) of inorganic filler particles having a particle size in the range from 0.12 μm to 10 μm:

$$n_{B2,470\ nm}-0.010<n_{A,470\ nm}<n_{B2,470\ nm}+0.035,$$

and/or where the following condition applies to the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.015<n_{B1,470\ nm}<n_{B2,470\ nm}+0.030.$$

4. The dental light-curable composition as claimed in claim 1, wherein the total amount (A) of free-radically polymerizable monomers is in the range from 21 to 34 percent by volume, based on the overall dental light-curable composition, and/or is in the range from 6 to 20 percent by weight, based on the overall dental light-curable composition, and/or the total amount (B1) of nonaggregated and nonagglomerated inorganic filler particles having a particle size in the range from 7 to 70 nm is in the range from 13 to 27 percent by volume based on the overall dental light-curable composition, and/or is in the range from 10 to 66 percent by weight based on the overall dental light-curable composition, and/or the total amount (B2) of inorganic filler particles having a particle size in the range from 0.12 μm to 10 μm is in the range from 42 to 60 percent by volume, based on the overall dental light-curable composition, and/or is in the range from 28 to 70 percent by weight, based on the overall dental light-curable composition, and/or the total amounts (A), (B1) and (B2) of the dental light-curable composition add up to at least 95 percent by volume based on the overall dental light-curable composition, and/or at least 95 percent by weight based on the overall dental light-curable composition.

5. The dental light-curable composition as claimed in claim 1, wherein the total amount (B1) of nonaggregated and nonagglomerated inorganic filler particles having a particle size in the range from 7 to 70 nm consists of filler particles which (i) have an identical physical composition and (ii) have additionally been surface-modified.

6. The dental light-curable composition as claimed in claim 1, wherein the total amount (B2-p2) of inorganic filler particles having a particle size in the range from 0.40 μm to 10 μm, consists of an amount of filler particles of the same physical composition that have been surface-modified, where this amount of filler particles has a refractive index $n_{B2,\ 470\ nm}$ in the range from 1.450 to 1.560, or consists of a mixture of two, three or more than three portions of filler particles, where the filler particles within each portion have an identical physical composition and have been surface-modified, but the filler particles from different portions have a different physical composition, where each of these portions on its own has a refractive index $n_{B2,\ 470\ nm}$ in the range from 1.450 to 1.560.

7. The dental light-curable composition as claimed in claim 1, wherein the total amount (A) of free-radically polymerizable monomers is selected such that a polymeric material is obtainable by light-curing thereof that has a refractive index increased by at least 0.015 determined at a wavelength of 589 nm.

8. The dental light-curable composition as claimed in claim 1, comprising, in addition to the total amounts (A), (B1), (B2) and (C), a total amount (D) of colorants selected from the group consisting of inorganic color pigments, organic color pigments and dyes.

9. The dental light-curable composition as claimed in claim 8, wherein the following condition applies to the translucence $T_{Col}$ of this dental light-curable composition after curing compared to the translucence $T_{NoCol}$ of a dental light-curable composition of otherwise identical composition that does not comprise any additional colorants:

$$35\% > T_{NoCol} - T_{Col} > 5\%,$$

and/or wherein the total amount (D) of the one or more colorants forms a proportion by volume of not more than 800 ppm based on the overall dental light-curable composition, and/or forms a proportion by mass of not more than 2000 ppm based on the overall dental light-curable composition, and/or wherein the dental light-curable composition after curing has a translucence $T_{col}$ of less than 28%.

10. The dental light-curable composition as claimed in claim 1, wherein the total amount of all inorganic particles having a particle size of not more than 0.12 μm in the composition has an average volume-based particle size of less than 70 nm, determined by means of dynamic light scattering.

11. The dental light-curable composition as claimed in claim 1, wherein the following conditions apply to the color values of the dental light-curable composition after curing, determined according to EN ISO 11664-4:

$$55.0 < L^* < 80.0, \text{ and}$$

$$-1.5 < a^* < 4.5, \text{ and}$$

$$5.0 < b^* < 20.0.$$

12. The dental light-curable composition as claimed in claim 1, comprising, in addition to the total amounts (A), (B1), (B2) and (C), a total amount (E) of one, two, three or more than three auxiliaries that are not colorants, where the auxiliaries in the total amount (E) are selected from the group consisting of:

rheological auxiliaries, polymerization initiators that are not photoinitiators, chemical compounds as catalysts or constituents of catalyst systems, stabilizers, especially UV and daylight stabilizers, inhibitors, activators, molecular weight regulators, preservatives, interface-active substances, biocides, organic polymers and oligomers and compounds having high molecular weights, thickeners, and dental medicaments.

13. A dental restoration or cured dental material obtainable by light curing of a dental light-curable composition as claimed in claim 1.

14. A process for producing the dental light-curable composition of claim 1, comprising the following steps:

(i) selecting the total amount (A) of free-radically polymerizable monomers, the total amount (B1) of nonaggregated and nonagglomerated inorganic filler particles having a particle size in the range from 7 to 70 nm, the total amount (B2) of inorganic filler particles having a particle size in the range from 0.12 μm to 10 μm, and the total amount (C) of photoinitiators, with the following applicable criteria for selection of the total amounts (A), (B1) and (B2):

the total amount (A) of free-radically polymerizable monomers has a refractive index $n_{A,\ 470\ nm}$ in the range from 1.470 to 1.560, the total amount (B1) of nonaggregated and nonagglomerated inorganic filler particles having a particle size in the range from 7 to 70 nm has a refractive index $n_{B1,\ 470\ nm}$ in the range from 1.460 to 1.570, the total amount (B2) of inorganic filler particles having a particle size in the range from 0.12 μm to 10 μm has a refractive index $n_{B2,\ 470\ nm}$ in the range from 1.450 to 1.560, for the refractive indices of the total amount (A) of free-radically polymerizable monomers and the total amount (B1) of nonaggregated and nonagglomerated inorganic filler particles having a particle size in the range from 7 to 70 nm:

$$n_{B1,470\ nm}-0.025<n_{A,470\ nm}<n_{B1,470\ nm}+0.030,$$

for the refractive indices of the total amount (A) of free-radically polymerizable monomers and the total amount (B2) of inorganic filler particles having a particle size in the range from 0.12 μm to 10 μm:

$$n_{B2,470\ nm}-0.015<n_{A,470\ nm}<n_{B2,470\ nm}+0.040,$$

for the refractive indices of the total amount (B1) of nonaggregated and nonagglomerated inorganic filler particles having a particle size in the range from 7 to 70 nm and the total amount (B2) of inorganic filler particles having a particle size in the range from 0.12 μm to 10 μm:

$$n_{B2,470\ nm}-0.020<n_{B1,470\ nm}<n_{B2,470\ nm}+0.035,$$

(ii) producing or providing the selected total amounts (A), (B1), (B2) and (C), (iii) mixing the total amounts (A), (B1), (B2) and (C) produced or provided in step (ii) and optionally additionally a total amount (D) of colorants and/or a total amount (E) of one, two, three or more than three additional auxiliaries, so as to result in the dental light-curable composition.

15. A method of producing a visible restoration in the anterior region or for filling of a cavity in the posterior region, comprising the following steps:

(i) producing or providing a dental light-curable composition as claimed in claim 1, (ii) applying the dental light-curable composition produced or provided to the part of the teeth to be restored or filled, (iii) curing the dental light-curable composition applied by irradiating with light in the wavelength range from 450 nm to 490 nm.

* * * * *